US012725615B2

(12) United States Patent
Pieri et al.

(10) Patent No.: US 12,725,615 B2
(45) Date of Patent: Sep. 1, 2026

(54) BILINGUAL MEDICAL MIXTURE OF EXPERTS LARGE LANGUAGE MODEL

(71) Applicant: MOHAMED BIN ZAYED UNIVERSITY OF ARTIFICIAL INTELLIGENCE, Abu Dhabi (AE)

(72) Inventors: Sara Pieri, Abu Dhabi (AE); Sahal Shaji Mullappilly, Abu Dhabi (AE); Fahad Khan, Abu Dhabi (AE); Rao Anwer, Abu Dhabi (AE); Salman Khan, Abu Dhabi (AE); Timothy Baldwin, Abu Dhabi (AE); Hisham Cholakkal, Abu Dhabi (AE)

(73) Assignee: MOHAMED BIN ZAYED UNIVERSITY OF ARTIFICIAL INTELLIGENCE, Abu Dhabi (AE)

(*) Notice: Subject to any disclaimer, the term of this patent is extended or adjusted under 35 U.S.C. 154(b) by 132 days.

(21) Appl. No.: 18/905,019

(22) Filed: Oct. 2, 2024

(65) Prior Publication Data

US 2025/0266037 A1 Aug. 21, 2025

Related U.S. Application Data

(60) Provisional application No. 63/555,634, filed on Feb. 20, 2024.

(51) Int. Cl.
*G10L 15/22* (2006.01)
*G06F 40/40* (2020.01)

(Continued)

(52) U.S. Cl.
CPC .............. *G10L 15/22* (2013.01); *G06F 40/40* (2020.01); *G10L 15/183* (2013.01); *G16H 70/00* (2018.01)

(58) Field of Classification Search
None
See application file for complete search history.

(56) References Cited

U.S. PATENT DOCUMENTS 9,959,271 B1 * 5/2018 Goyal ..................... G06F 40/51
2012/0253786 A1 * 10/2012 Al-Omari ............... G06F 40/10 704/8

(Continued)

FOREIGN PATENT DOCUMENTS

CN 117112759 A 11/2023
CN 117708307 A 3/2024

OTHER PUBLICATIONS

Liu et al., "MOELoRA: An MOE-based Parameter Efficient Fine-Tuning Method for Multi-task Medical Applications", Oct. 21, 2023 ( Year: 2023).*

(Continued)

*Primary Examiner* — Nafiz E Hoque
(74) *Attorney, Agent, or Firm* — Oblon, McClelland, Maier & Neustadt, L.L.P.

(57) ABSTRACT

A computer-implemented system and computer instructions stored on non-transitory computer readable medium for bilingual medical inquiry in both Arabic and English, including multiple-choice question answering, open-ended question answering, and multi-turn question answering. The system and instructions use a mixture of experts large language model (MOE LLM) having a router network connected to multiple expert networks. The MOE LLM is trained with medical domain data and is used to receive the input bilingual text in a format for a medical inquiry, and output text in a format of a response to the medical inquiry, in sequence. The system and instructions incorporate an English-to-Arabic translation pipeline having a language translation model to generate Arabic language medical (Continued)

instruction sets from English language medical instructions, for large scale use in Arabic and English medical inquiry.

17 Claims, 17 Drawing Sheets

(51) Int. Cl.
*G10L 15/183* (2013.01)
*G16H 70/00* (2018.01)

(56) References Cited

U.S. PATENT DOCUMENTS

2018/0068662 A1* 3/2018 Schlippe ................. G10L 25/90
2020/0192982 A1 6/2020 Luqman et al.

OTHER PUBLICATIONS

Jiang et al., “Mixtral of Experts”, Jan. 8, 2024 (Year: 2024).*
Jiang (Year: 2024).*
Liu (Year: 2023).*
Abdennour Boulesnane, et al., “DZchatbot: A Medical Assistant Chatbot in the Algerian Arabic Dialect using Seq2Seq Model”, 2022 4th International Conference on Pattern Analysis and Intelligent Systems (PAIS); Nov. 17, 2022, 9 pages.

* cited by examiner (a) English-Arabic Training Data (a) Frequent Words

| Data | Samples | Avg. Turns | #Tokens |
|---|---|---|---|
| QA | 423.8 K | 1.00 | 131.8 K |
| MCQA | 638.1 K | 1.00 | 342.5 M |
| Chat | 249.7 K | 4.72 | 158.0 M |
| Total | 1311.6 K | 1.71 | 632.3 M |

+
506
EXZPER
504
EXZPERT
504
EXZPERT
504
ROUTER
502
500

Hello BiMediX. I've been experiencing recurring headaches for the past few weeks, and they seem to be getting more frequent.

I see. Headaches can have various causes. Can you please provide more details about your symptoms? For example, where is the pain located and how would you describe the pain?

الألم يحدث في الغالب على جانبي الرأس، أحيانًا على جانب واحد فقط. إنه ألم نابض يمكن أن يستمر لعدة ساعات. الضوء والضوضاء يبدو أنهما يجعلانه أسوأ

شكرًا لك على المعلومات المفصلة. استنادًا إلى أعراضك، يبدو أنك قد تعاني من صداع الشقيقة. صداع الشقيقة يتميز عادة بألم نابض في جانب واحد أو كلا الجانبين من الرأس، ويمكن أن يزيد الضوء والضوضاء من شدتها. من المهم أن نأخذ في الاعتبار أن هناك أسبابًا أخرى محتملة لأعراضك، لذا قد نحتاج إلى إجراء مزيد من التقييم. هل لاحظت أي عوامل محددة تثير هذه الصداع؟

Yes, I've been under a lot of stress at work lately, and my sleep hasn't been great.

Stress and inadequate sleep can definitely contribute to headaches. It's important to manage your stress levels and prioritize getting enough restful sleep. In the meantime, I can recommend some over-the-counter pain relievers such as ibuprofen or acetaminophen to help alleviate your symptoms. However, I would strongly advise scheduling an appointment with your primary care physician for a thorough evaluation and further guidance. They may recommend additional tests or treatments based on your specific situation.

FIG. 8

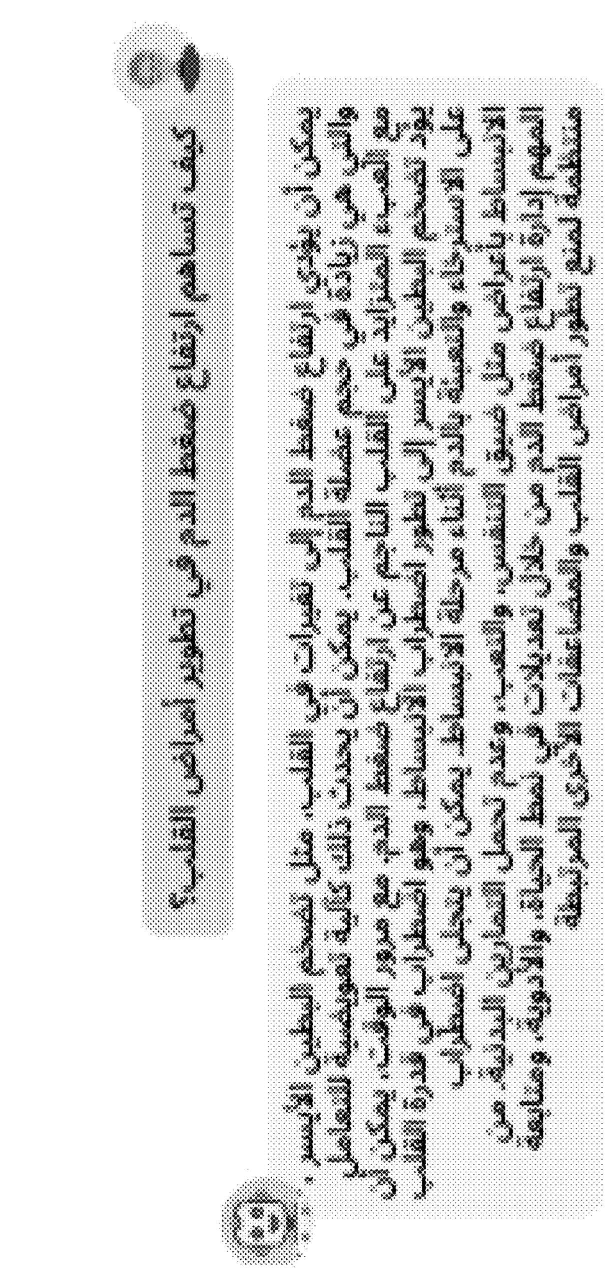
FIG. 9D

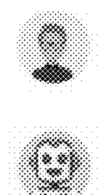

How would you differentiate between Autism Spectrum Disorder and Rett Syndrome in a young child, considering the nuances in developmental milestones and neurobehavioral patterns?

Autism Spectrum Disorder (ASD) and Rett Syndrome are both neurodevelopmental disorders, but they have distinct features. In general, ASD is characterized by impaired social interaction and communication, as well as restricted and repetitive behaviors. Rett Syndrome, on the other hand, is a rare genetic disorder that primarily affects females and is characterized by regression of developmental milestones, loss of purposeful hand skills, and development of repetitive hand movements. While both conditions can present with similar symptoms, the regression of developmental milestones and loss of purposeful hand skills are more specific to Rett Syndrome. Additionally, a genetic test known as the methylation-specific PCR for MECP2 can be used to confirm the diagnosis of Rett Syndrome.

FIG. 10A

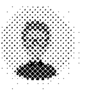

In a case of severe pancreatitis, how do you decide between conservative management and surgical intervention, taking into account the patient's overall condition and comorbidities?

The decision between conservative management and surgical intervention in a case of severe pancreatitis takes into account the patient's overall condition, comorbidities, and potential complications. In cases of mild pancreatitis, conservative management is usually sufficient. However, in cases of severe pancreatitis, surgical intervention may be necessary if there is a concern for complications such as necrotizing pancreatitis, infected pancreatic necrosis, or abscess formation. The patient's overall condition and comorbidities should be considered when making this decision.

FIG. 10B

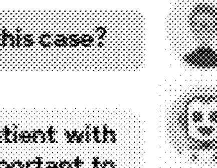
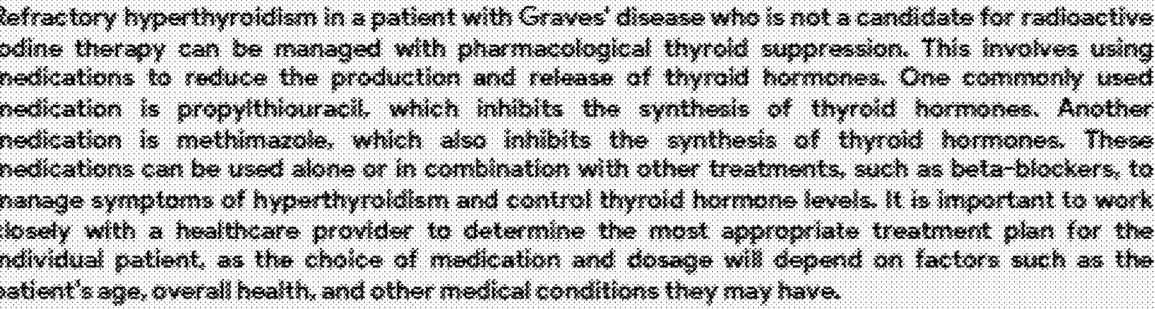
FIG. 10C

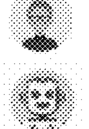
FIG. 11

BILINGUAL MEDICAL MIXTURE OF EXPERTS LARGE LANGUAGE MODEL

CROSS-REFERENCE TO RELATED APPLICATIONS

This application claims the benefit of priority to provisional application No. 63/555,634 filed Feb. 20, 2024, the entire contents of which are incorporated herein by reference.

STATEMENT REGARDING PRIOR DISCLOSURE BY THE INVENTORS

Aspects of this technology are described in an article Pieri, Sara, Sahal Shaji Mullappilly, Fahad Shahbaz Khan, Rao Muhammad Anwer, Salman Khan, Timothy Baldwin, and Hisham Cholakkal. "BiMediX: Bilingual Medical Mixture of Experts LLM." arXiv preprint arXiv:2402.13253 (2024), and is herein incorporated by reference in its entirety.

BACKGROUND

Technical Field

The present disclosure is directed to a bilingual medical large language model, method and system, and in particular a training method for the bilingual medical large language model and a chat assistant method and system for interactive bilingual conversation for medical inquiry.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Large Language Models (LLMs) demonstrate excellent ability to understand instructions, generate human-like text, and tackle unseen or complex tasks, rendering them valuable for a broad range of applications. LLMs have demonstrated excellent ability in several applications, including content generation, language translation, search and recommendation, virtual assistants, sentiment analysis, question answering, and classification. LLMs have been created with multilingual capabilities that extend across numerous languages, including English, German, Spanish, French, Italian, Polish, Romanian, Swedish, and more. This allows for seamless integration of language translation into various types of applications, especially those requiring a deep understanding of multiple languages. Among the applications, virtual assistants can engage in conversations, referred to as chat, providing a more human-like interaction.

The language translation ability of LLMs has the potential to impact the medical field. LLMs can provide fast and accurate translations to many languages, effectively enabling both healthcare providers and patients to participate in clinical decision-making regardless of their native language. In addition, virtual assistant-based LLMs have the potential to impact the medical field by offering virtual chat support across diverse medical departments to enhance diagnostic accuracy. However, despite the promise of LLMs in healthcare, the medical domain poses distinct challenges, including the necessity for domain-specific data and expertise to ensure accurate interpretations, as well as concerns regarding transparency and bias. Furthermore, before LLMs can be applied in the medical domain, central conditions such as safety, validity and ethical concerns must be addressed.

Proprietary models such as OpenAI's GPT-3.5 and GPT-4, alongside Google's Flan-PaLM, Med-PaLM and Med-PaLM 2 have demonstrated impressive performances in English medical benchmarks. Large language models for medical applications are generally described in Hyung Won Chung, Le Hou, Shayne Longpre, Barret Zoph, Yi Tay, William Fedus, Yunxuan Li, Xuezhi Wang, Mostafa Dehghani, Siddhartha Brahma, et al. 2022. Scaling instruction-finetuned language models. arXiv preprint arXiv: 2210.11416; Karan Singhal, Shekoofeh Azizi, Tao Tu, S Sara Mahdavi, Jason Wei, Hyung Won Chung, Nathan Scales, Ajay Tanwani, Heather Cole-Lewis, Stephen Pfohl, et al. 2022. Large language models encode clinical knowledge. arXiv preprint arXiv:2212.13138; and Karan Singhal, Tao Tu, Juraj Gottweis, Rory Sayres, Ellery Wulczyn, Le Hou, Kevin Clark, Stephen Pfohl, Heather Cole-Lewis, Darlene Neal, et al. 2023. Towards expert-level medical question answering with large language models. arXiv preprint arXiv:2305.09617. Nonetheless, the scarcity of public medical information, alongside concerns regarding use of personal medical information and data privacy, motivate the development of open-source alternatives to proprietary models. These open-source alternatives aim for customization, transparent evaluation, and safe clinical integration.

Early open medical language models, in particular, enhanced BERT-style models for medical purposes, leverage the PubMed corpus for either continuous pre-training or specific domain training from scratch. Discussion of some open medical language models is in Jinhyuk Lee, Wonjin Yoon, Sungdong Kim, Donghyeon Kim, Sunkyu Kim, Chan Ho So, and Jaewoo Kang. 2020. Biobert: a pre-trained biomedical language representation model for biomedical text mining. *Bioinformatics,* 36(4):1234-1240; Kexin Huang, Jaan Altosaar, and Rajesh Ranganath. 2019. Clinicalbert: Modeling clinical notes and predicting hospital readmission. arXiv preprint arXiv:1904.05342; Iz Beltagy, Kyle Lo, and Arman Cohan. 2019. Scibert: A pretrained language model for scientific text. arXiv preprint arXiv: 1903.10676; Yu Gu, Robert Tinn, Hao Cheng, Michael Lucas, Naoto Usuyama, Xiaodong Liu, Tristan Naumann, Jianfeng Gao, and Hoifung Poon. 2021. Domain-specific language model pretraining for biomedical natural language processing. *ACM Transactions on Computing for Healthcare* (*HEALTH*), 3(1):1-23; and Hoo-Chang Shin, Yang Zhang, Evelina Bakhturina, Raul Puri, Mostofa Patwary, Mohammad Shoeybi, and Raghav Mani. 2020. Biomegatron: Larger biomedical domain language model. arXiv preprint arXiv:2010.06060. Subsequent research has enhanced bidirectional systems to incorporate link structures and knowledge graphs. Some examples of subsequent research can be found in Michihiro Yasunaga, Jure Leskovec, and Percy Liang. 2022b. Linkbert: Pretraining language models with document links. arXiv preprint arXiv: 2203.15827; and Michihiro Yasunaga, Antoine Bosselut, Hongyu Ren, Xikun Zhang, Christopher D Manning, Percy S Liang, and Jure Leskovec. 2022a. Deep bidirectional language-knowledge graph pretraining. *Advances in Neural Information Processing Systems,* 35:37309-37323.

Building on the success of generative pre-trained transformer (GPT) model versions, some studies have tailored GPT-2 based models to medical and scientific literature.

Tuning of GPT models for medical and scientific end uses is discussed in Elliot Bolton, David Hall, Michihiro Yasunaga, Tony Lee, Chris Manning, and Percy Liang. BioMedLM: a domain-specific large language model for biomedical text. crfm.stanford.edu/2022/12/15/biomedlm.html; Renqian Luo, Liai Sun, Yingce Xia, Tao Qin, Sheng Zhang, Hoifung Poon, and Tie-Yan Liu. 2022. Biogpt: generative pre-trained transformer for biomedical text generation and mining. *Briefings in Bioinformatics,* 23(6):bbac409; and Ross Taylor, Marcin Kardas, Guillem Cucurull, Thomas Scialom, Anthony Hartshorn, Elvis Saravia, Andrew Poulton, Viktor Kerkez, and Robert Stojnic. 2022. Galactica: A large language model for science. arXiv preprint arXiv:2211.09085.

Other, later works such as MedAlpaca focus on finetuning large scale open-source LLMs such as LLaMA on a set of medical instructions. Examples of finetuning LLaMA on medical instructions are discussed in Tianyu Han, Lisa C Adams, Jens-Michalis Papaioannou, Paul Grundmann, Tom Oberhauser, Alexander Löser, Daniel Truhn, and Keno K Bressem. 2023. Medalpaca—an open-source collection of medical conversational ai models and training data. arXiv preprint arXiv:2304.08247; Hugo Touvron, Thibaut Lavril, Gautier Izacard, Xavier Martinet, Marie-Anne Lachaux, Timothée Lacroix, Baptiste Roziere, Naman Goyal, Eric Hambro, Faisal Azhar, et al. 2023a. Llama: Open and efficient foundation language models. arXiv preprint arXiv:2302.13971; and Hugo Touvron, Louis Martin, Kevin Stone, Peter Albert, Amjad Almahairi, Yasmine Babaei, Nikolay Bashlykov, Soumya Batra, Prajjwal Bhargava, Shruti Bhosale, et al. 2023b. Llama 2: Open foundation and fine-tuned chat models. arXiv preprint arXiv:2307.09288, each incorporated herein by reference in their entirety. ChatDoctor enhanced a LLaMA model on 100K clinical Q&As, incorporating knowledge retrieval capabilities. See Li Yunxiang, Li Zihan, Zhang Kai, Dan Ruilong, and Zhang You. 2023. Chatdoctor: A medical chat model fine-tuned on llama model using medical domain knowledge. arXiv preprint arXiv:2303.14070. Clinical-Camel has introduced question answering data with the Dialogue-Based Knowledge Encoding (DBKE) process, converting PubMed articles and MedQA into questions and descriptive answers. The DBKE process is described in Augustin Toma, Patrick R Lawler, Jimmy Ba, Rahul G Krishnan, Barry B Rubin, and Bo Wang. 2023. Clinical camel: An open-source expert-level medical language model with dialogue-based knowledge encoding. arXiv preprint arXiv:2305.12031. PMC-LLaMA and Meditron perform pre-training on PubMed content and medical texts, with further refinements on individual multiple choice question answering (MCQA) datasets. Training for medical MCQA is discussed in Chaoyi Wu, Xiaoman Zhang, Ya Zhang, Yanfeng Wang, and Weidi Xie. 2023. Pmc-llama: Further fine-tuning llama on medical papers. arXiv preprint arXiv:2304.14454; and Zeming Chen, Alejandro Hernández Cano, Angelika Romanou, Antoine Bonnet, Kyle Matoba, Francesco Salvi, Matteo Pagliardini, Simin Fan, Andreas Köpf, Amirkeivan Mohtashami, et al. 2023. Meditron-70b: Scaling medical pretraining for large language models. arXiv preprint arXiv:2311.6079. Med42 is an instruction-tuned LLaMA model for medical tasks, though the details of its training remain undisclosed. A discussion of Med42 is found in Clément Christophe, Avani Gupta, Nasir Hayat, Praveen Kanithi, Ahmed Al-Mahroogi, Prateek Munjal, Marco Pimentel, Tathagata Raha, Ronnie Rajan, and Shadab Khan. 2023.

Other approaches have emerged to bridge the gap in medical domain knowledge, which involve open-source medical LLM alternatives to proprietary models like ChatGPT. Discussion of some open-source medical models is provided in Zeming Chen, Alejandro Hernández Cano, Angelika Romanou, Antoine Bonnet, Kyle Matoba, Francesco Salvi, Matteo Pagliardini, Simin Fan, Andreas Köpf, Amirkeivan Mohtashami, et al. 2023. Meditron-70b: Scaling medical pretraining for large language models. arXiv preprint arXiv:2311.16079; Augustin Toma, Patrick R Lawler, Jimmy Ba, Rahul G Krishnan, Barry B Rubin, and Bo Wang. 2023. Clinical camel: An open-source expert-level medical language model with dialogue-based knowledge encoding. arXiv preprint arXiv:2305.12031; Chaoyi Wu, Xiaoman Zhang, Ya Zhang, Yanfeng Wang, and Weidi Xie. 2023. Pmc-llama: Further fine-tuning llama on medical papers. arXiv preprint arXiv:2304.14454; and Josh Achiam, Steven Adler, Sandhini Agarwal, Lama Ahmad, Ilge Akkaya, Florencia Leoni Aleman, Diogo Almeida, Janko Altenschmidt, Sam Altman, Shyamal Anadkat, et al. 2023. Gpt-4 technical report. arXiv preprint arXiv:2303.08774. However, among the leading medical LLMs in English, Med42-70B has not made its training data and resources available. A discussion of Med42 is found in Clément Christophe, Avani Gupta, Nasir Hayat, Praveen Kanithi, Ahmed Al-Mahroogi, Prateek Munjal, Marco Pimentel, Tathagata Raha, Ronnie Rajan, and Shadab Khan. 2023. Med42—a clinical large language model, incorporated herein by reference in its entirety. Meditron-70B, relies on separate fine-tuning for each evaluation dataset. This approach is likely to compromise the model's ability to serve as a unified solution with diverse interaction capabilities.

Regarding processing models in languages other than English, progress has been made in Arabic language processing models, including notable models such as AraT5 and AraBART. Discussion of AraT5 and AraBART are provided in El Moatez Billah Nagoudi, AbdelRahim Elmadany, and Muhammad Abdul-Mageed. 2021. Arat5: Text-to-text transformers for arabic language generation. arXiv preprint arXiv:2109.12068; and Moussa Kamal Eddine, Nadi Tomeh, Nizar Habash, Joseph Le Roux, and Michalis Vazirgiannis. 2022. Arabart: a pretrained arabic sequence-to-sequence model for abstractive summarization. arXiv preprint arXiv:2203.10945. In addition to these monolingual models, Arabic has been integrated into multilingual frameworks. A discussion of multilingual language frameworks is found in Teven Le Scao, Angela Fan, Christopher Akiki, Ellie Pavlick, Suzana Ilić, Daniel Hesslow, Roman Castagné, Alexandra Sasha Luccioni, Frangois Yvon, et al. 2022. Bloom: A 176b-parameter open-access multilingual language model. arXiv preprint arXiv:2211.05100; and Niklas Muennighoff, Thomas Wang, Lintang Sutawika, Adam Roberts, Stella Biderman, Teven Le Scao, M Saiful Bari, Sheng Shen, Zheng-Xin Yong, Hailey Schoelkopf, et al. 2022. Crosslingual generalization through multitask finetuning. arXiv preprint arXiv:2211.01786. In addition, the launch of the Jais model marked a substantial advancement as a general-purpose bilingual LLM for English and Arabic. A discussion of Jais is found in Neha Sengupta, Sunil Kumar Sahu, Bokang Jia, Satheesh Katipomu, Haonan Li, Fajri Koto, Osama Mohammed Afzal, Samta Kamboj, Onkar Pandit, Rahul Pal, et al. 2023. Jais and jais-chat: Arabic-centric foundation and instruction-tuned open generative large language models. arXiv preprint arXiv:230816149. Additionally, many of the foundational large language models demonstrate the ability to reply in Arabic, despite their limited exposure to the language during pre-training. However, these generic models lack sufficient medical domain knowledge, making them ill-equipped for medical applications in either or both Arabic and English languages.

Still, when it comes to the medical domain, most of the leading open-source medical LLMs are limited to the English language. As such, most open-source medical LLMs are insufficient for understanding and interacting in training resource-constrained languages such as Arabic. As mentioned above, example open-source medical LLMs have been described. Despite Arabic's potential to cater to a population of more than 400 million people, it remains underrepresented in the medical LLM literature. In contrast, English has been said to be the third most spoken language in the world, with 379 million speaking it as their first language.

Arabic language is substantially different from English language. Translation between English and Arabic is very difficult by human, and much more difficult by machine translators. Arabic texts are written and read from right to left, using a cursive script, compared to English which is written using Latin script and read from left to right. In Arabic, there is no distinction between lower and upper cases and the rules on the use of punctuation are looser compared to English. Arabic has six individual phonemes that are not found in the English language. These phonemes are a reason why Arabic to English translation is difficult. English uses more consonant clusters (phoneme groupings) when forming words. Arabic differentiates between females and males in its sentence structure, words, verbs, pronouns. It even has specifications for you and they in singular, plural, male and female forms. In Arabic, word roots do not contain vowels. To form the words, vowel infixes between a series of consonants are added. The change in the meaning of the word depends on the use of a vowel infix.

Basic sentence structures of English and Arabic are substantially different. English only has verbal sentences. Arabic has verbal and nominal sentences. Arabic's nominal sentences do not need verbs and typically comprise two nouns only. Arabic has four different types of sentences: verbal, functional, nominal and non-functional.

Arabic uses Unicode scripts that have special orthographic rules that require certain combinations of letterforms to be combined into special ligature forms. The rules governing ligature formation in Arabic can be quite complex.

Such unique features of Arabic, such as its distinctive script and less conventional right-to-left writing format present challenges in the development of Arabic or English-Arabic bilingual medical LLMs. Relatively low amount of medical literature may not be a significant problem for researches, as these researchers may be educated in both English and Arabic. However, persons using the Internet and interacting with chatbots may be more apt to use their native language, especially when it comes to inquiries about medical issues. Even bilingual persons may mix words or sentences between the two languages, such as when they are familiar with a way of talking about a certain topic, or name of an illness, as an example. Subsequentially, a shortage of information in the medical domain in Arabic can be a substantial problem, especially in the case of development of a chatbot for bilingual interaction. The unavailability of large-scale medical training data in Arabic, and subsequently the lack of a comprehensive benchmark to evaluate Arabic medical LLMs is a substantial hinderance.

Accordingly, it is one object of the present disclosure to provide methods and systems for a bilingual medical LLM with seamless conversational capabilities in both English and Arabic. It is a further object to implement a bilingual medical LLM as a chat agent with superior performances on various benchmarks in both English and Arabic. The bilingual medical LLM model has an object to conduct consistent medical interactions irrespective of the language used. The chat agent can conduct interactions, including multi-turn interactions essential for follow-up inquiries with human patients, multiple-choice question answering and open-ended question answering. An object is a pipeline that facilitates the compilation of an instruction-tuning dataset and a comprehensive benchmark for evaluating Arabic healthcare LLMs and Arabic-English Bilingual LLMs. An object is a parameter-efficient architecture with a goal to reduce required computation resources.

SUMMARY

An aspect of the present disclosure is a computer-implemented system for medical inquiry, that can include a textual input device for inputting bilingual text in both Arabic and English; processing circuitry configured with a mixture of experts large language model (MOE LLM) having a router network connected to a plurality of expert networks which are arranged with independent weight parameters, wherein the MOE LLM is trained with medical domain data and is configured to receive the input bilingual text in a format for a medical inquiry, and output text in a format of a response to the medical inquiry; and a display device for displaying the input bilingual text and the response to the medical inquiry in sequence.

In a further aspect of the present disclosure, a non-transitory computer-readable storage medium including computer executable instructions, wherein the instructions, when executed by a computer, cause the computer to perform a method of medical inquiry, the method can include inputting, a textual input device, bilingual text in both Arabic and English; training, by processing circuitry, a mixture of experts large language model (MOE LLM) having a router network connected to a plurality of expert networks which are arranged with independent weight parameters, wherein the training is with medical domain data; receiving, by the MOE LLM, the bilingual text in a format for a medical inquiry; outputting, by the MOE LLM, text in a format of a response to the medical inquiry; and displaying, by a display device, the received bilingual text and the response to the medical inquiry in sequence.

In a further aspect of the present disclosure, a smart speaker system for medical inquiry, can include a speech input device for inputting bilingual speech in both Arabic and English; speech processing circuitry for converting the bilingual speech into bilingual text; processing circuitry configured with a mixture of experts large language model (MOE LLM) having a router network connected to a plurality of expert networks which are arranged with independent weight parameters, wherein the MOE LLM is trained with medical domain data and is configured to receive the bilingual text in a format for a medical inquiry, and output text in a format of a response to the medical inquiry; and a display device for displaying the received bilingual text and the response to the medical inquiry in sequence.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 8 illustrates a screen displaying examples of medical-related conversations performed seamlessly in both English and Arabic;

FIGS. 9C and 9D illustrate displays for open-ended medical-related questions and responses performed with the chat assistant;

FIGS. 10A, 10B and 10C illustrate displays for further open-ended medical-related questions and responses performed with the chat assistant;

FIG. 11 illustrates a display for a medical-related conversation in Arabic;

DETAILED DESCRIPTION

Figure 1:
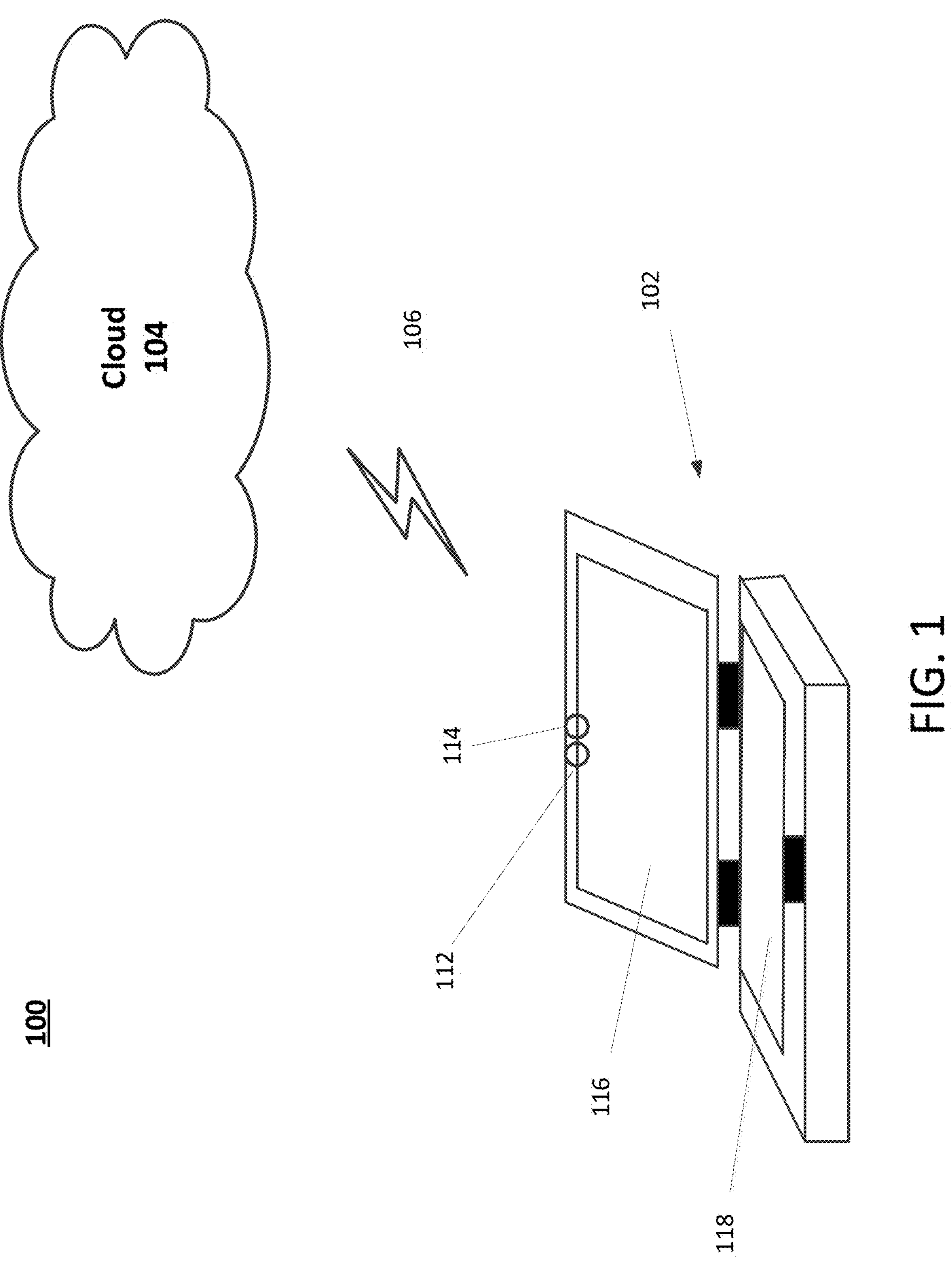
FIG. 1 is a diagram of a system for training a bilingual medical large language model and for a chat assistant for interactive bilingual conversation for the medical domain.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

As mentioned above, the unique features of Arabic, such as its distinctive script and less conventional right-to-left writing format, as well as the unavailability of large-scale medical training data in Arabic, and the lack of a comprehensive benchmark to evaluate Arabic medical LLMs, present particular challenges in the development of Arabic or English-Arabic bilingual medical LLMs.

Several solutions to these problems have been considered. One approach can be to construct one model for one language and another model for a second language, and branch to the one model or the second model depending on the language being input. However, this approach runs the risk of different responses for the different language models. Also, there is a problem where some responses may not be generated for one of the language models due to insufficient training for the one language. Another approach may be to construct a medical diagnostic model in one language and include one or more language translation models, or a multilingual language model as an interface to the medical diagnostic model. However, this later approach results in a very large and complex use of computational resources.

The present solution involves creation of a comprehensive Arabic-English bilingual instruction set named BiMed1.3M comprising over 1.3 million instructions. The solution uses the BiMed1.3M dataset to train a mixture of experts architecture, which is implemented with fewer training resources than conventional mixture of experts models, allowing for more efficient performance.

Aspects of this disclosure are directed to a system, device, and method for comprehensive medical interactions, including conversations, multiple choice question answer (MCQA), and open-ended question answering (QA) consistently in both English and Arabic languages. The implementation of a semi-automated translation pipeline, coupled with human refinement, ensures the high quality of English-to-Arabic translations.

An aspect is a bilingual medical mixture of experts LLM having consistent and seamless interaction capabilities in both English and Arabic languages. The model facilitates various medical interactions, including multi-turn chats essential for follow-up inquiries with human patients, multiple-choice question answering and open-ended question answering.

An aspect is a semi-automated iterative translation pipeline, incorporating a human verification step to ensure high-quality translation of English medical text into resource-constrained Arabic. This pipeline facilitates the compilation of instruction-tuning dataset and a comprehensive benchmark for evaluating Arabic healthcare LLMs and Arabic-English Bilingual LLMs.

An aspect is a comprehensive Arabic-English bilingual instruction set named BiMed1.3M comprising over 1.3 million instructions, resulting in a total of over 632 million healthcare specialized tokens. The dataset comprises open-ended question-and-answer, multiple-choice question answering, and over 200 k synthesized multi-turn chats rooted in authentic medical content. The integration of multi-turn conversations allows for the creation of a chatbot agent capable of conducting follow-up inquiries with human patients. The dataset maintains a 1:2 Arabic to English ratio across diverse medical interactions.

An aspect is parameter-efficient fine-tuning of routing and expert layers in a mixture of experts architecture, such as Mixtral, using the BiMed1.3M dataset, that requires fewer training resources compared to conventional mixture of experts models described in Med42 and Chen et al. See Albert Q Jiang, Alexandre Sablayrolles, Antoine Roux, Arthur Mensch, Blanche Savary, Chris Bamford, Devendra Singh Chaplot, Diego de las Casas, Emma Bou Hanna, Florian Bressand, et al. 2024. Mixtral of experts. arXiv preprint arXiv:2401.04088; and Zeming Chen, Alejandro Hernández Cano, Angelika Romanou, Antoine Bonnet, Kyle Matoba, Francesco Salvi, Matteo Pagliardini, Simin Fan, Andreas Köpf, Amirkeivan Mohtashami, et al. 2023. Meditron-70b: Scaling medical pretraining for large language models. arXiv preprint arXiv:2311.16079, each incorporated herein by reference in their entirety. Bilingual instruction tuning with the BiMed1.3M dataset leads to an average absolute 10% gain over the base mixtral on bilingual evaluations.

Sparse expert models, of which, Mixture-of-Experts (MoE) is the most popular variant, are neural networks where a set of the parameters are partitioned into "experts", each with unique weights. During training and inference, the models route input examples to specific expert(s) weights. As a result, each example only interacts with a subset of the network parameters. Because only a fraction of the experts are used for each example, the amount of computation may remain small relative to the total model size. With respect to hardware, experts reside on different accelerators and the input data is dynamically dispatched to and fetched from the accelerators.

The present solution goes a step further by incorporating parameter efficient fine tuning (PEFT). PEFT methods allow fine-tuning using only a small number of extra weights in the model while freezing most of the parameters of the pre-trained network. A PEFT method used herein, QLoRA-based PEFT described below, involves quantizing a transformer model to 4-bit precision and using paged optimizers to handle memory spikes.

FIG. 1 is a diagram of a system for training a bilingual medical large language model and for a chat assistant for interactive bilingual conversation for the medical domain.

FIG. 1 is a diagram for a system for a chat assistant for interactive bilingual conversation for the medical domain. The chat assistant may be accessed through the Internet or may be part of a hospital or clinic local computer network. The chat assistant may be part of a Web site or a mobile application (App). In any case, the system requires processing capability for text, but may include capability for handling sound and video.

The system 100 includes a computing device 102, which could include a laptop computer, tablet computer, smartphone, or desktop computer, and can also include a smart TV. The computing device 102 includes a textual input device 118 for inputting bilingual text in both Arabic and English. The computing device 102 may provide a setup process to enable each language and is configured to toggle between languages by way of an input command, such as through a mouse click on a menu item or a button press. A new language such as Arabic can be set up for a particular operating system, such as Windows, MacOS, Android, IOS, to name a few, and input device such as a bilingual keyboard or keyboard App on a tablet or smartphone with a touchscreen.

The computing device 102 can include one or more camera units 114, and may include a microphone 112 and internal speakers.

The computing device 102 may include a connection 106 to an external system, such as a cloud service 104 or a network system. The computing device 102 may include communication circuitry for high-speed communication with external devices as well as the cloud service. In one embodiment, the software for the system 100 may be configured as a software application stored in a repository such as GitHub, and made available for download.

Figure 2:
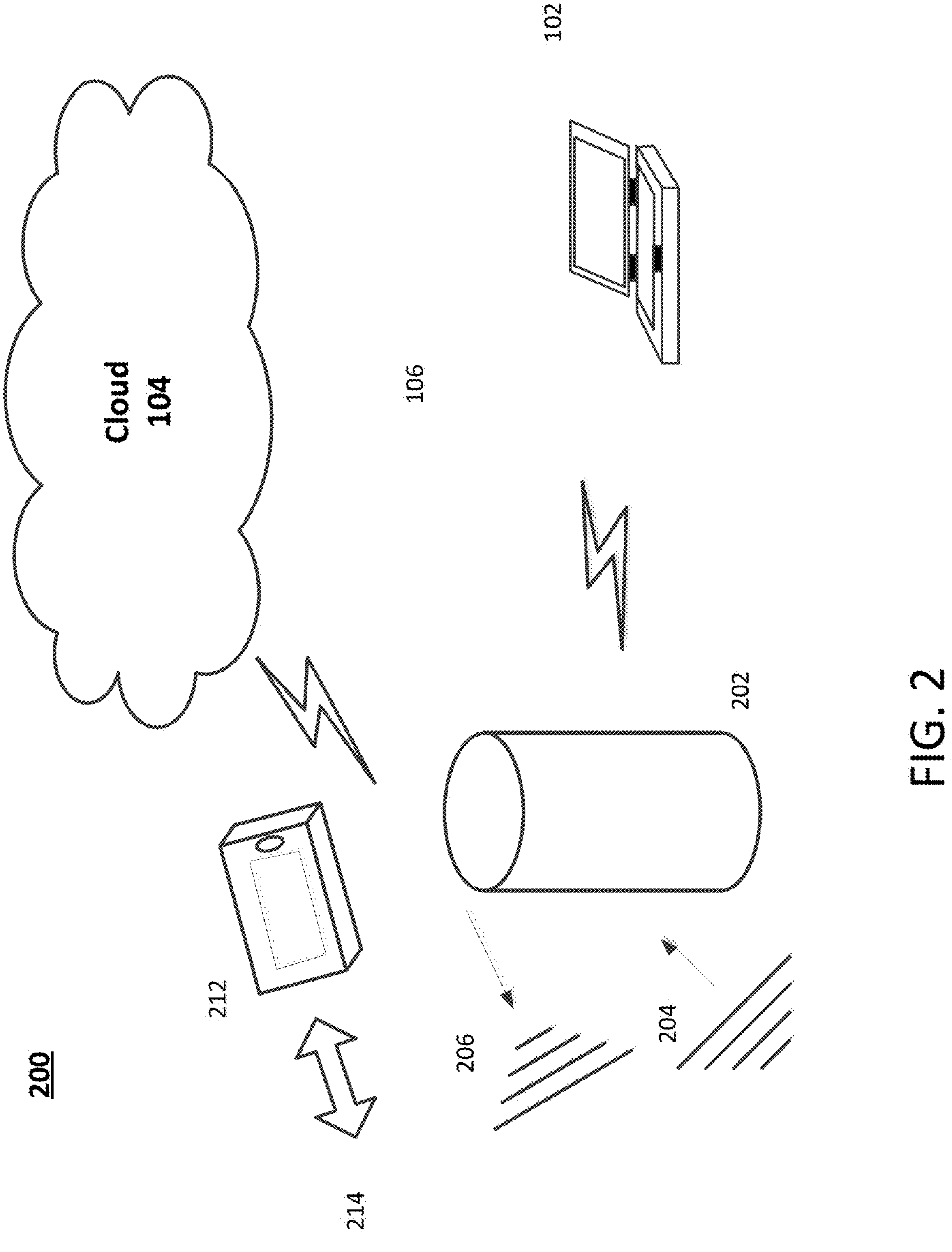
FIG. 2 is a diagram of a system for a verbal embodiment of a chat assistant for interactive bilingual conversation for the medical domain.

FIG. 2 is a diagram of a system for a verbal embodiment of a chat assistant for interactive bilingual conversation for the medical domain. In an embodiment, the system may be implemented with a smart speaker or other audio input/output device for interaction by way of speech. A person may input commands, instructions, questions, and other context by speaking 204 to the smart speaker 202 or other audio input/output device, such as a smartphone 212. The smart speaker 202 or other device 212 can respond with its own speech 206 as an output.

Similar to the system of FIG. 1, the system 200 of FIG. 2 may include communication with a cloud service 104 or other external network system. A display device 102 may be configured to work in communication with the smart speaker 202 to provide display capability in conjunction with, or as an alternative to, the speech output 206.

The smart speaker 202 or other audio input/output device may use the cloud service 104 or computing resources in the other network for performing speech recognition and speech output. In an embodiment, the smart speaker 202 or other audio input/output device may include processing circuitry for converting the speech signals into text for a respective language. The chat assistant logic can be configured as a backend process. In one embodiment, the software for the system 200 may be configured as an application or mobile App, or as an Alexa Skill. The software application or mobile App may be stored in a cloud-based online store, such as Google Play or Apple Store, and made available for download.

A bilingual healthcare chat assistant, a comprehensive bilingual dataset named BiMed1.3M is described that encompasses diverse medical interactions such as multiple-choice question answers (MCQAs), open-ended questions, and multi-turn chat conversations, in both English and Arabic. This bilingual dataset is created by first compiling English instruction. Subsequently, a semi-automated English-to-Arabic translation pipeline is described, which enables the obtaining of high-quality Arabic medical benchmarks and instruction sets. The generated Arabic instructions are then combined with English instructions to obtain the BiMed1.3M bilingual dataset. Finally, a model and instruction-tuning strategy is provided.

BiMed1.3M: Bilingual Dataset with Diverse Medical Interactions

The growing need for AI-driven medical assistants, proficient across a spectrum of NLP tasks, highlights the necessity for comprehensive datasets. In particular, the ability to deliver concise answers is critical for evaluating model performance, yet the functionality for engaging in chat is essential for practical deployment. This holds particular significance in the healthcare domain, where multiple turns of interaction with further inquiries about symptoms, examinations, and preexisting conditions are often necessary. To this end, an English instruction set is compiled as detailed below.

Compiling English Instruction Set

At first, a dataset in English is compiled encompassing three types of medical interactions: multiple-choice question answering (MCQA), which focuses on specialized medical knowledge and reasoning for definitive answers; open question answering (QA), that includes real-world consumer questions; and multi-turn chat conversations for dynamic exchanges. For the first two categories, various existing sources are combined into a unified collection of question-answer pairs, as detailed in Table 1. For the multi-turn chat component, realistic conversations are generated grounded on MCQA scenarios as described below.

TABLE 1

Summary of collected data sources for multiple-choice (MCQA) and open question answering (QA).

| Dataset | Description |
|---|---|
| | Multiple-Choice Question Answering (MCQA) |
| PubMedQA | Closed-answer questions from medical abstracts in PubMed research papers. |
| MedMCQA | Multiple-choice questions from the Indian AIIMS and NEET PG medical entrance exams. |
| MedQA | Multiple-choice questions from the USMLE for U.S. medical licensing. |
| | Question Answering (QA) |
| HealthCareMagic | Specialist-patient Q&As crawled from HealthCareMagic. |
| iCliniq | Physician-patient Q&As from the iCliniq consultation site. |
| Medical Meadow | Q&A pairs from Anki flashcards and Wikidoc's medical textbooks and Patient Information. |
| UMLS | Q&As on medical term meanings and entity relationships from knowledge graphs. |
| LiveQA | Annotated consumer health questions from the National Library of Medicine (NLM). |
| MedicationQA | Annotated consumer medications inquiries from MedlinePlus. |

Some question answering datasets are described in Qiao Jin, Bhuwan Dhingra, Zhengping Liu, William W Cohen, and Xinghua Lu. 2019. Pubmedqa: A dataset for biomedical research question answering. arXiv preprint arXiv: 1909.06146; Ankit Pal, Logesh Kumar Umapathi, and Malaikannan Sankarasubbu. 2022. Medmcqa: A large-scale multi-subject multi-choice dataset for medical domain question answering. In *Conference on Health, Inference, and Learning*, pages 248-260. PMLR; Di Jin, Eileen Pan, Nassim Oufattole, Wei-Hung Weng, Hanyi Fang, and Peter Szolovits. 2021. What disease does this patient have? a large-scale open domain question answering dataset from medical exams. *Applied Sciences,* 11(14):6421; Yunxiang et al., 2023; Han et al., 2023; Wu et al., 2023; Asma Ben Abacha, Eugene Agichtein, Yuval Pinter, and Dina Demner-Fushman. 2017. Overview of the medical question answering task at trec 2017 liveqa. In TREC, pages 1-12; and Asma Ben Abacha, Yassine Mrabet, Mark Sharp, Travis R Goodwin, Sonya E Shooshan, and Dina Demner-Fushman. 2019. Bridging the gap between consumers' medication questions and trusted answers. In *MedInfo*, pages 25-29, each incorporated herein by reference in their entirety.

MCQA-grounded Multi-turn Chat Generation: To generate realistic and engaging multi-turn conversations that are medically accurate, ChatGPT's conversational flow is used together with publicly available medical MCQAs (multiple-choice question answers). ChatGPT is used to simulate potential doctor-patient dialogues based on MCQAs. The chat creation process involves using ChatGPT to draft messages for both the user and the AI assistant in a dialogue format. Inputs from the PubmedQA, MedQA, and MedMCQA datasets are provided with specific directives to generate multi-turn discussions relevant to the medical question answer pairs (MCQA). A prompt template is employed to define the format and criteria alongside the input question, generating conversation transcripts for both parties (doctor and patient) until a logical conclusion is reached.

The MCQA-grounded multi-turn interactions produced by the disclosed approach are generally thorough and insightful, covering aspects like symptom inquiries and further information requests. Based on this approach, more than 200,000 high-quality multi-turn medical dialogues are produced, each linked to a specific MCQA, collectively comprising over 74 million tokens.

Following the generation of multi-turn dialogues, the dataset comprehensively encompasses multiple-choice question answering (MCQA), open question answering (QA), and dynamic chat conversations (Chats)—totaling over 860,000 instruction-tuning data in English. Additional details on the diversity and composition of the data are provided below. Moreover, various publicly available medical benchmark datasets in English are leveraged to evaluate the performance of the trained model, as elaborated below.

Next, details are provided of the semi-automated iterative translation pipeline to generate medical evaluation benchmarks and instruction sets tailored for the resource-constrained Arabic language.

Semi-Automated Iterative Translation

Figure 3:
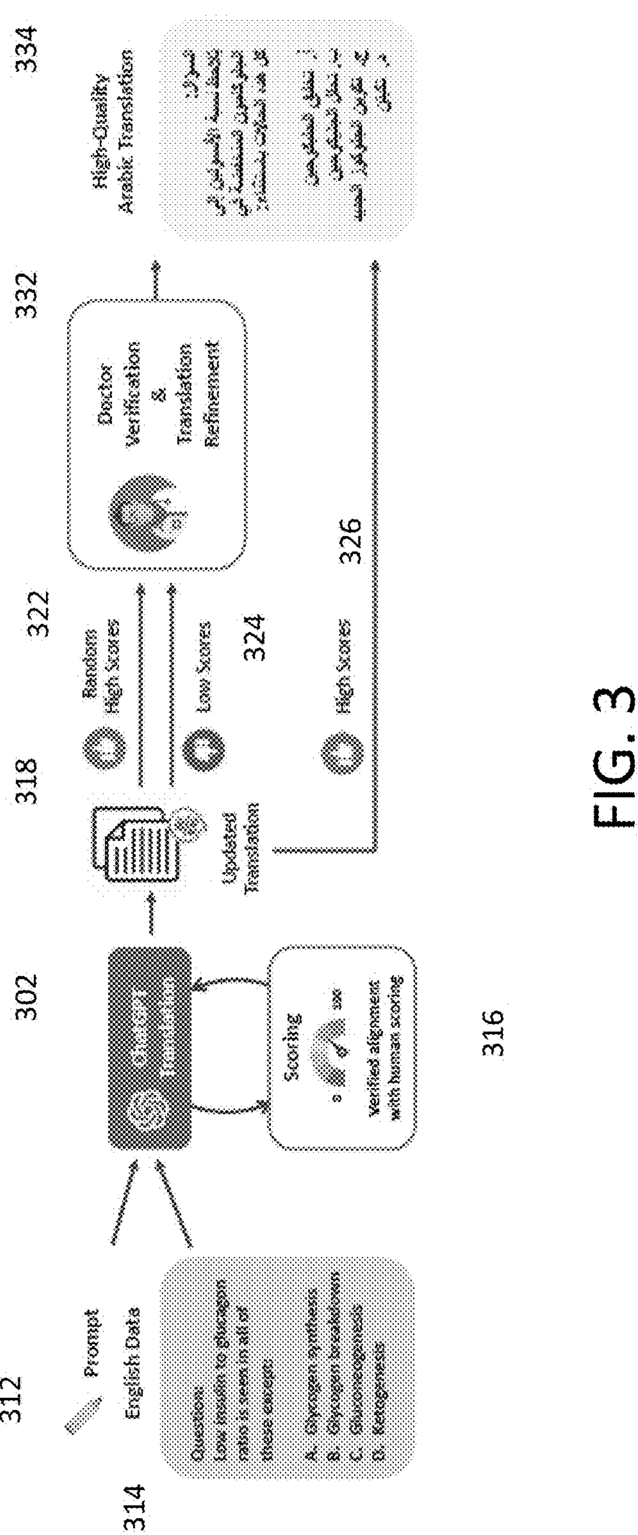
FIG. 3 is a flow diagram for a semi-automated, iterative translation pipeline featuring human alignment, in accordance with an exemplary aspect of the disclosure.

A semi-automated iterative translation pipeline is shown in FIG. 3. At first, English to Arabic translation is performed using ChatGPT 302, which delivers high-quality translations by considering the entire input English text 3145 as context. ChatGPT 302 outputs a quality value for the quality of the translated Arabic text relative to its original English version. A scoring operation 316 is performed which assigns scores ranging from 0 to 100, directly proportional to the translation quality value. This scoring operation 316 aims to quantitatively assess the fidelity and clarity of translations, ensuring the accurate preservation of technical terminology and specifics.

In a preferred embodiment, the scoring is performed with ChatGPT. Arabic speakers check that the scoring is appropriately capturing technical terminology and content. The initial scores obtained from ChatGPT may require further alignment with the scores provided for the same samples by native Arabic speakers. By understanding the failures in translation quality on those mismatched samples, the prompts given to the model are improved for computing the scores. This Arabic speaker-supported adjustment of prompts is repeated for several iterations to develop a reliable prompt (model instruction) that produces scores better aligned with human expert scores. The final prompt, given a pair of English text and its corresponding Arabic translation, asks the model to output a score between 1-100 assessing the quality of the translation. The evaluation explicitly (through prompt) asks the model to score based on completeness, consistency and alignment with the original English text, correct preservation of technical terms and details in the corresponding Arabic. The scoring system allows for iterative improvement of the ChatGPT original translations by resubmitting the translation request to ChatGPT.

MEANT is one metric used to evaluate the quality of machine translation and may be used to determine the quality value of a machine translation. MEANT is based on the idea that the most important aspect of a machine translation is its ability to convey the intended meaning of the source text.

The MEANT metric uses semantic role labeling (SRL) to analyze the structure and meaning of the sentence. SRL, also known as shallow semantic parsing or slot-filling, labels words or phrases in a sentence that represent a semantic role. These labels follow a semantic analysis of the sentence and enable such questions as "who did what to whom" to be answered.

MEANT is calculated by combining the scores obtained from semantic role labeling, lexical similarity, and role filler estimation. The process starts by using a shallow semantic parser to analyze both the machine translation output and the reference sentence. Then, the semantic frame is aligned using maximum weighted bipartite matching based on the lexical similarity of the predicate. The lexical similarity and role filler are estimated using word embeddings. Finally, the weighted F-score is calculated by matching the role label and role filler.

Additionally, the alignment of these scores to human preferences is verified with the assistance of native Arabic speakers. In an embodiment, the verification includes an evaluation to assess safety, validity, or ethical aspects of translated language. The verification may be performed indirectly through the automated scoring system and from the subset evaluated from Arabic speaking medical doctors, which can be tasked with translation refinement if necessary.

For translations that score below a predefined threshold, a refinement process is initiated. This involves providing ChatGPT 302 with the original English text, along with the current translations and their scores as feedback. ChatGPT is prompted to update the translation to ensure optimal consistency and alignment with the English originals. This feedback loop iteratively improves the translation quality through successive revisions. Translations that score above the predefined threshold are output 334.

Furthermore, in order to scale to a greater quantity of high-quality translations, samples with initially low scores are also refined to increase their scores and translation quality through this automated procedure. To accomplish this further refinement, in 332, all translations with scores below a threshold 324 are subject to a thorough manual verification and refinement process performed by a medical professional fluent in Arabic. In addition, to ensure high quality, a random subset of translations with high scores 322 is also sampled for professional review. The random selection process is performed using known random number generation functions, which in Python, can include randrange( ) and choice( ), to name a few. This iterative translation process ensures that final Arabic translations 334 adhere to rigorous academic and clinical standards and can scale up for very high quantities of Arabic translations in the medical domain.

Bilingual Benchmark & Instruction Set

Creation of Medical Benchmark: To evaluate the accuracy and applicability of Arabic medical AI models, the English medical evaluation benchmarks are translated into Arabic using the aforementioned iterative translation procedure. By providing a high-quality Arabic medical benchmark aligned with its English counterpart, a fundamental step is established in bridging the linguistic divide in model evaluation and comparison, thereby offering a valuable asset for further research.

These Arabic benchmarks are combined with the original English evaluation benchmarks to create an English-Arabic bilingual benchmark. This allows assessment of the linguistic capabilities of the bilingual model as well as its medical domain knowledge.

Bilingual Instruction Set: 444,995 English samples have been translated into Arabic, covering all three types of medical interactions. A bilingual approach is adopted, mixing Arabic and English in a 1:2 ratio. This approach led to the creation of an extensive bilingual instruction tuning dataset that integrates both languages. Consequently, an English-Arabic bilingual dataset named BiMed1.3M is compiled, which is 1.5 times larger than the English counterpart, comprising more than 1,311,000 samples.

Figures 4A, 4B, 4C:
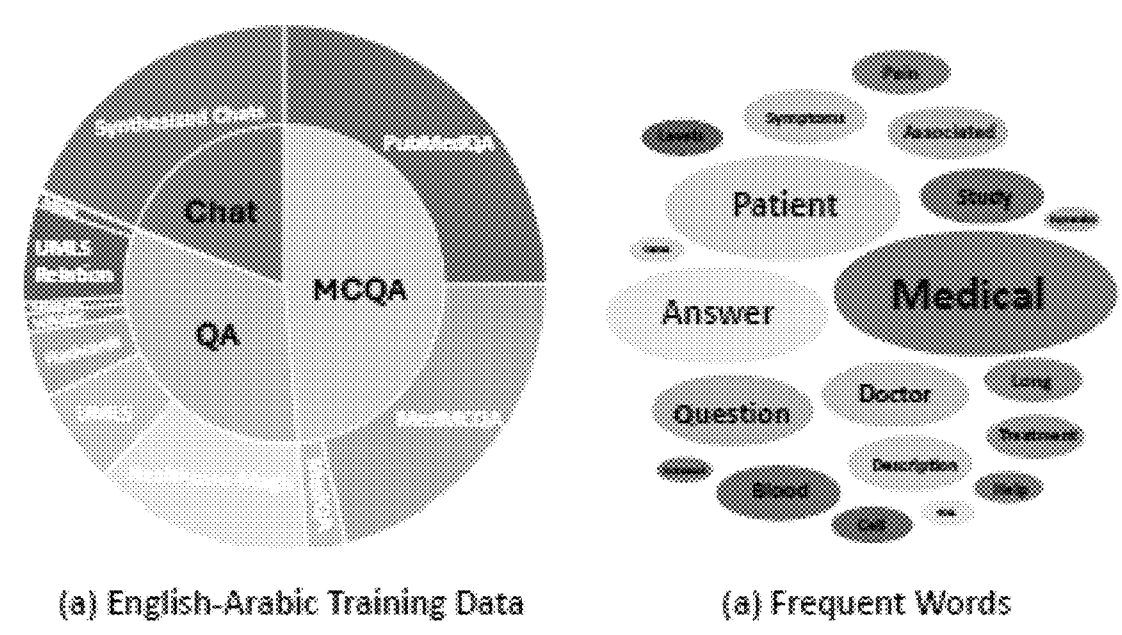
FIGS. 4A, 4B, 4C illustrate an overview of an English-Arabic training dataset, in accordance with an exemplary aspect of the disclosure.

Details of the BiMed1.3M training data are illustrated in Table 1, above, and FIGS. 4A, 4B, and 4C. FIG. 4A is a pie chart of the data distribution. FIG. 4B illustrates results of a word frequency analysis.

FIG. 4C is a table of statistics of the BiMed1.3M training data across QA, MCQA, and Chat (with more than one turn of exchanges) totaling 623M tokens and the approximately 1.3M samples. As noted above, this bilingual dataset, derived from translating approximately 50% of the English dataset into Arabic, is 1.5 times larger due to its 2:1 English-to-Arabic content ratio.

Next the model and its bilingual medical instruction tuning are described.

Bilingual Medical Instruction Tuning of Mixture of Experts LLM

Figure 5:
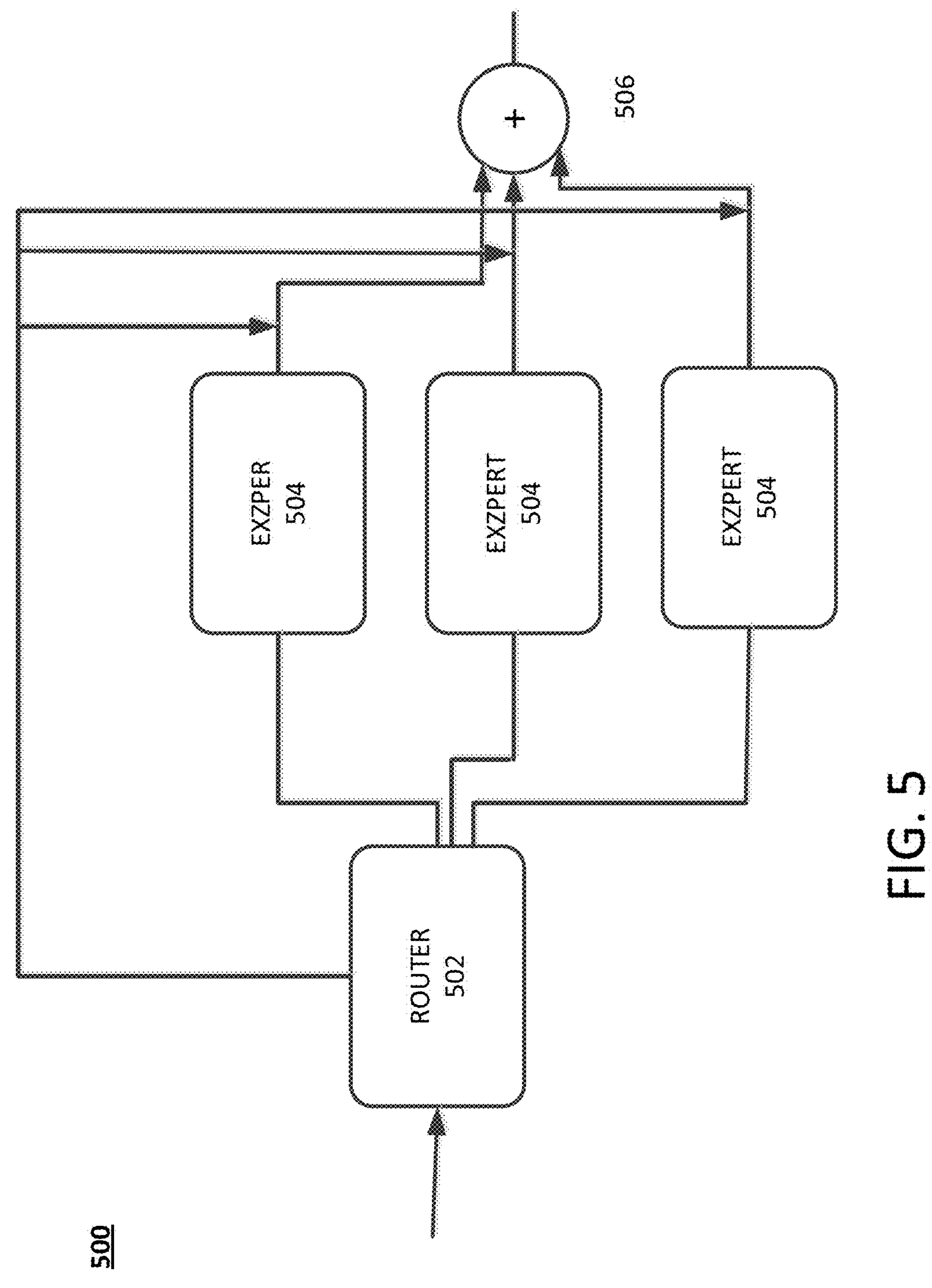
FIG. 5 is a block diagram for a mixture of experts model, in accordance with an exemplary aspect of the disclosure.

FIG. 5 is a block diagram for a mixture of experts model. A Mixture of Experts model 500 includes a router 502 that feeds into a number of experts 504, whose outputs are later combined 506. Mixtral is a Mixture of Experts (MoE) based architecture that achieves impressive performance on generic NLP benchmarks in English. Mixtral enables substantial scaling of model size within the same computational budget as traditional dense models. Unlike traditional dense feed-forward network layers, Mixtral employs a set number of "experts" 504 in a sparse manner, replacing the FFN layers in dense networks. Additionally, a gate network or router 502 is employed to direct input tokens to appropriate experts based on learned parameters.

While Mixtral offer advantages such as improved inference times over dense models, the model faces challenges in Arabic-English bilingual medical applications due to limited medical domain knowledge and Arabic language capabilities. To address these challenges, Arabic-English bilingual medical instruction tuning of Mixtral MoE architecture is performed using the BiMed1.3M dataset.

Figure 6:
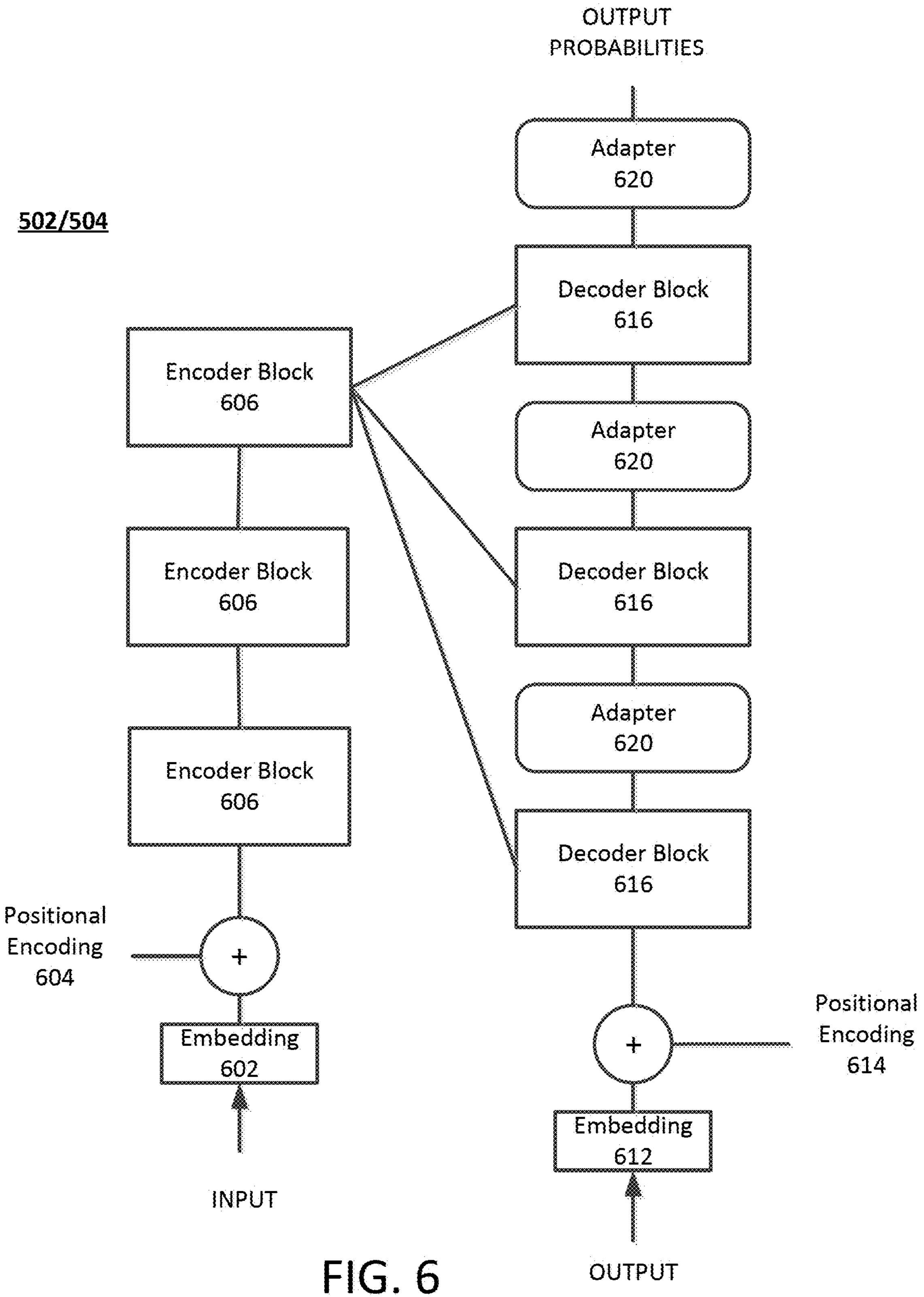
FIG. 6 is a block diagram for a transformer with QLoRA adapters, in accordance with an exemplary aspect of the disclosure.

FIG. 6 is a block diagram for a transformer with QLoRA adapters. Performing conventional supervised fine-tuning of a mixture of experts model, such as Mixtral, requires substantial computational resources and often encounters challenges in carefully tuning the expert layers and the routing network leading to generalization issues. To this end, Parameter-Efficient Finetuning (PEFT) techniques are employed to adapt the pre-trained mixture of experts model with minimal computational resources while ensuring high performance and adaptability. Types of PEFT are described in Edward J Hu, Yelong Shen, Phillip Wallis, Zeyuan Allen-Zhu, Yuanzhi Li, Shean Wang, Lu Wang, and Weizhu Chen. 2021. Lora: Low-rank adaptation of large language models. arXiv preprint arXiv:2106.09685; Xiang Lisa Li and Percy Liang. 2021. Prefix-tuning: Optimizing continuous prompts for generation. arXiv preprint arXiv:2101.00190; Tim Dettmers, Artidoro Pagnoni, Ari Holtzman, and Luke Zettlemoyer. 2023. Qlora: Efficient finetuning of quantized llms. arXiv preprint arXiv:2305.14314; and Jiang et al., 2024, each incorporated herein by reference in their entirety.

In this disclosure, the Mixture of Experts architecture has been fine-tuned as a bilingual medical chat assistant by utilizing the BiMed1.3M dataset for instruction tuning. The Mixture of Experts architecture used herein incorporates QLoRA-based PEFT training. It has been determined that including the adapters only in the decoder of each transformer model is optimal for training the bilingual medical chat assistant. Subsequently, QLoRA adapters 620 are connected to the decoder layers 616 of the transformer, in each of the experts 504 and the routing network 502.

Figure 7:
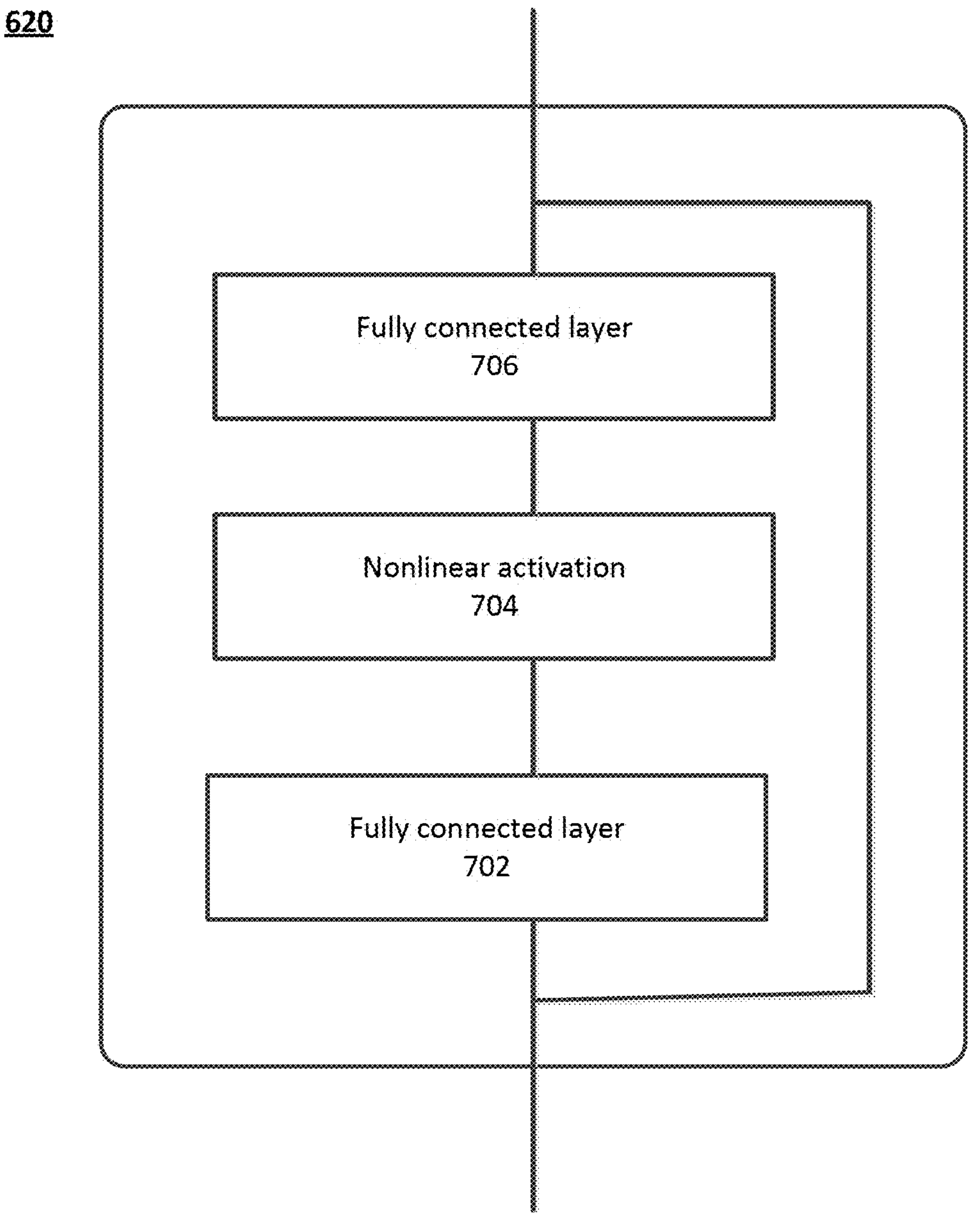
FIG. 7 is a block diagram for an adapter, in accordance with an exemplary aspect of the disclosure.

FIG. 7 is a block diagram for an adapter 620. In QLoRA-based training, tuning with adapter modules involves adding a small number of new parameters to a model by injecting new layers (e.g., adapters 620) into the transformer 502/504, in which only the new layers are trained on a downstream task. In adapter tuning the parameters of the original network are frozen and therefore can be shared by many tasks.

An adapter module/layer 620 itself can include a fully connected layer 702, a non-linear activation layer 704, and another fully connected layer 706. In an illustrative example, the first fully connected layer 702 projects a 1024-dimensional input down to 24 dimensions, and the second fully connected layer 706 projects it back into 1024 dimensions.

Moreover, to align with the conversational style in the BiMed1.3M dataset, for both English and Arabic instructions, the Vicuna data format "conversations": ["from": "human/AI," "value": " . . . " ], is used calculating loss exclusively for the AI's responses within the dialogue script. This loss calculation approach is described in Wei-Lin Chiang, Zhuohan Li, Zi Lin, Ying Sheng, Zhanghao Wu, Hao Zhang, Lianmin Zheng, Siyuan Zhuang, Yonghao Zhuang, Joseph E Gonzalez, et al. 2023. Vicuna: An open-source chatbot impressing gpt-4 with 90%* chatgpt quality. See vicuna.lmsys. org (accessed 14 Apr. 2023), incorporated herein by reference in its entirety. Unlike alternative approaches cited above, the approach refrains from conducting additional medical pre-training before instruction-tuning it on the medical dataset.

In summary, through careful instruction tuning of the routing network and experts in the Mixtral decoder using our BiMed1.3M dataset, enhanced medical domain capabilities is achieved in both Arabic and English languages. This includes proficiency in multiple-choice question answering, open-ended question answering, and realistic multi-turn question answering between our BiMediX model and the user (e.g., patient), making it suitable for deployment as a bilingual medical chatbot.

FIG. 8 illustrates a screen displaying examples of medical-related conversations performed seamlessly in both English and Arabic. BiMedX facilitates various medical interactions, including multi-turn chats essential for follow-up inquiries with human patients. BiMedX demonstrates advanced interactive capabilities, such as soliciting further details from the patient and seamlessly switch languages based on patient input while maintaining the continuity of the conversation. The Arabic text translates as follows: User: The pain occurs mostly on both sides of the head, sometimes on only one side. It is a throbbing pain that can last for several hours. Light and noise seem to make it worse. BiMediX: Thank you for the detailed information. Based on your symptoms, it sounds like you may have a migraine. Migraine headaches are usually characterized by a throbbing pain on one or both sides of the head, and can be triggered or increased in intensity by light and noise. It is important to consider that there are other possible causes for your symptoms, so we may need to do further evaluation. Have you notices any specific factors that trigger these headaches?

Figure 9A:
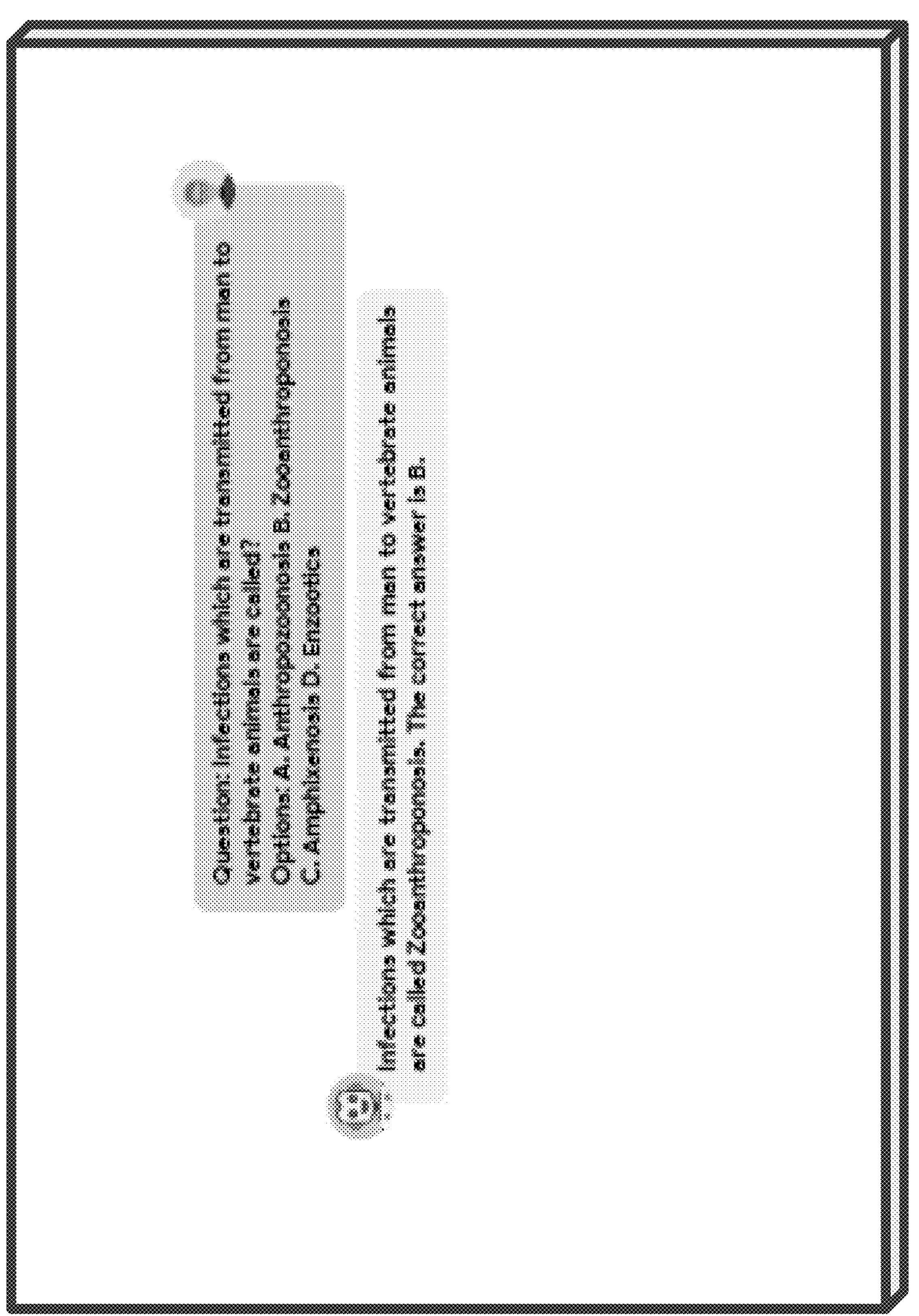
FIGS. 9A and 9B illustrate displays for medical-related multiple-choice questions and answers performed with the chat assistant.
Figure 9B:
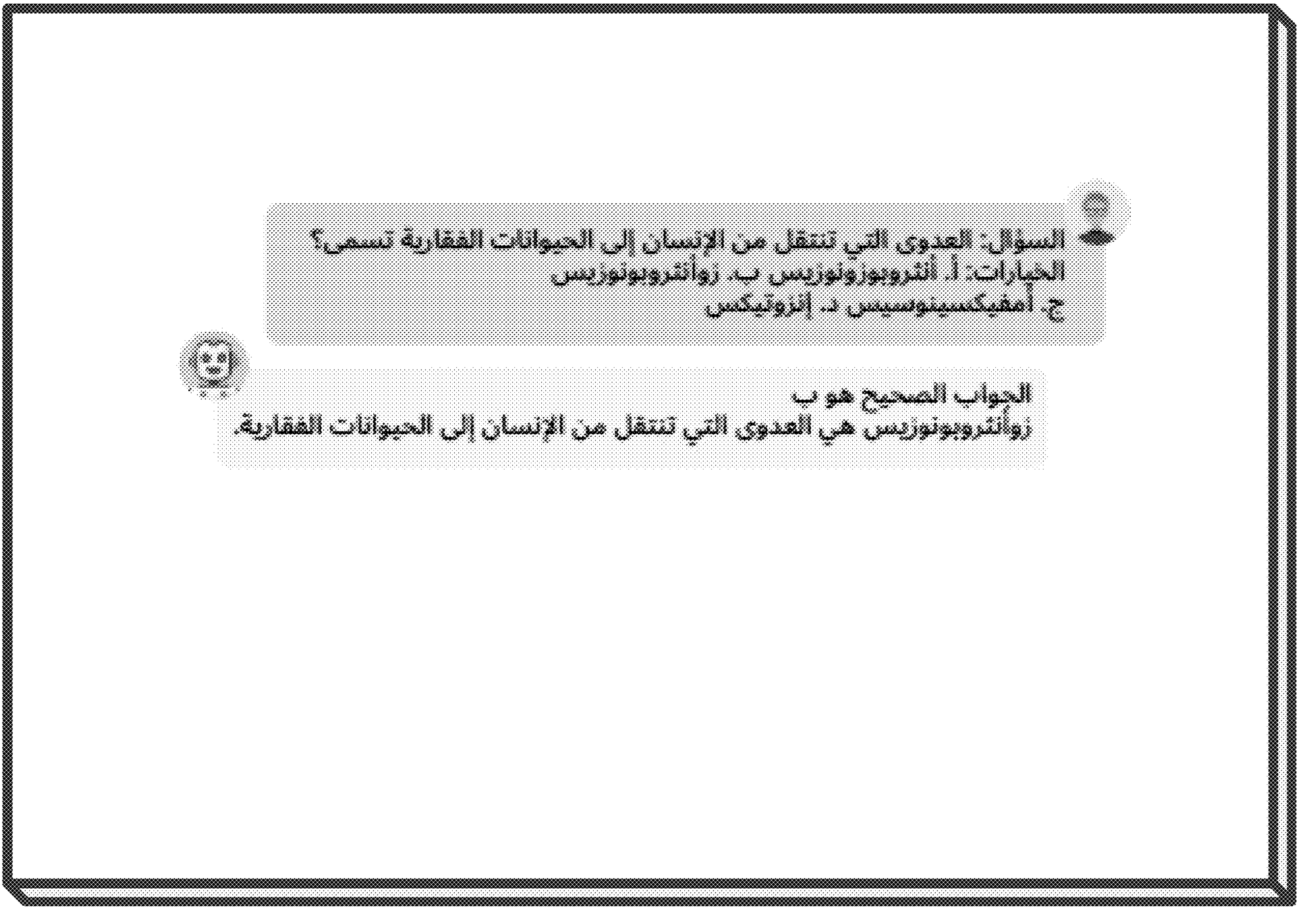
Figure 9C:

English, Arabic language capabilities of BiMediX are further illustrated in FIGS. 9A to 9D. FIGS. 9A and 9B illustrate displays for medical-related multiple-choice questions and answers performed with the chat assistant. FIGS. 9C and 9D illustrate displays for open-ended medical-related questions and responses performed with the chat assistant.

Experiments

Experimental Settings

In an embodiment, BiMediX is built upon mixtral (Mixtral-8x7B) base network, a sparse mixture of experts language model. Mixtrel is described in Jiang et al., 2024. This model extends the Mistral-7B architecture, featuring a unique design with each layer hosting eight "expert" feed-forward blocks. Mistral is described in Albert Q Jiang, Alexandre Sablayrolles, Arthur Mensch, Chris Bamford, Devendra Singh Chaplot, Diego de las Casas, Florian Bressand, Gianna Lengyel, Guillaume Lample, Lucile Saulnier, et al. 2023. Mistral 7b. arXiv preprint arXiv:2310.06825, incorporated herein by reference in its entirety. A router network determines which two experts will process each token, and their outputs are merged. Consequently, it handles 47 billion parameters, with fewer than 13 billion active during inference. This model features a hidden state dimension of 14,336, a context window capable of accommodating 32,768 tokens, 32 layers, 32 attention heads, and a vocabulary size of 32,000.

Mixtral is fine-tuned using QLoRA, a low-rank adaptation technique, by incorporating a set of learnable low-rank adapter weights into both the experts and the routing network. This adaptation applies to q, k, and v, setting the rank to 128 and the a parameter to 64. Consequently, this approach results in the training of approximately 4% of the original parameters. The disclosed bilingual model underwent training on roughly 632 million tokens sourced from the Arabic-English corpus and there are 288 million English tokens to train English model. The training hyper-parameters included an effective batch size of 16 with two gradient accumulation steps and utilized the AdamW optimizer with a learning rate of 0.0002, cosine learning rate schedule, and ten warmup steps. The exemplary model implementation leveraged PyTorch, along with the Deepspeed and ZeRO packages, with gradient checkpointing. These packages are described in Adam Paszke, Sam Gross, Francisco Massa, Adam Lerer, James Bradbury, Gregory Chanan, Trevor Killeen, Zeming Lin, Natalia Gimelshein, Luca Antiga, et al. 2019. Pytorch: An imperative style, high-performance deep learning library. Advances in neural information processing systems, 32; Jeff Rasley, Samyam Rajbhandari, Olatunji Ruwase, and Yuxiong He. 2020. Deepspeed: System optimizations enable training deep learning models with over 100 billion parameters. In Proceedings of the 26th ACM SIGKDD International Conference on Knowledge Discovery & Data Mining, pages 3505-3506; Samyam Rajbhandari, Jeff Rasley, Olatunji Ruwase, and Yuxiong He. 2020. Zero: Memory optimizations toward training trillion parameter models. In SC20: International Conference for High Performance Computing, Networking, Storage and Analysis, pages 1-16. IEEE; and Tianqi Chen, Bing Xu, Chiyuan Zhang, and Carlos Guestrin. 2016. Training deep nets with sublinear memory cost. arXiv preprint arXiv:1604.06174, each incorporated herein by reference in their entirety. Our BiMedix is trained for two epochs with eight A100 (80 GB) GPUs, requiring only 35 hours for the training.

Quantitive Evaluation

In the literature, evaluating medical language models predominantly involves multiple-choice question-answering tasks, with accuracy as the performance metric. The disclosed model is evaluated using the EleutherAI evaluation framework1.

Medical Benchmarks

The analysis incorporates multiple prominent benchmarks in medical multiple-choice question-answering. Two of these datasets are sourced directly from the National Board of Medical Examiners (NBME), responsible for the assessments required for medical licensure in the U.S.

(i) PubMedQA is a question-answering dataset derived from biomedical research papers on PubMed. Given a question sourced from the title of a research paper and a context from the abstract, the task is to provide an answer in the form of 'yes', 'no', or 'maybe', mirroring the conclusion of the paper. Building on prior research, the examination focuses on the PQA-L subset of PubMedQA, consisting of 1,000 manually annotated QA pairs sourced from PubMed. Answering these questions with accuracy requires thorough reasoning over the biomedical contexts and quantitative data analysis.

(ii) MedMCQA is a multiple-choice dataset constructed from questions featured in the Indian AIIMS and NEET PG medical entrance exams. It covers a broad spectrum of medical subjects, evaluating both professional domain knowledge and language comprehension. The dataset includes a test set of 4,183 questions, each with four options.

(iii) MedQA is a dataset comprising multiple-choice questions from medical board examinations in the US, Mainland China, and Taiwan. It features two types of questions: concise sentences to assess specific knowledge and extended paragraphs that detail a patient's condition. The analysis used herein concentrates on the English portion (USMLE), containing 1,273 samples for testing purposes. Engaging with this benchmark involves multiple stages of reasoning and evidence retrieval.

(iv) The Medical MMLU (Massive Multitask Language Understanding) is a group of six datasets that compiles 1,089 test questions with four options related to different medical subjects. The six MMLU datasets are Clinical Knowledge (Cli-KG), College Biology (C-Bio), College Medicine (C-Med), Medical Genetics (Med-Gen), Professional Medicine (Pro-Med) & Anatomy (Ana).

All 7045 questions from the above English datasets are translated into Arabic using the disclosed semi-automated pipeline to create our Arabic and Bilingual evaluation benchmarks.

Results

Bilingual Evaluation: Here, BiMediX is evaluated on Arabic-English bilingual evaluation benchmark derived from evaluating results in both languages. Table 2 shows the BiMediX results against the base model, Mixtral-8x7B (not fine-tuned) and Jais-30B. The latter is a larger model designed specifically for the Arabic language and capable of functioning in both English and Arabic. BiMediX demonstrates superior performance across all benchmarks, achieving accuracy that is, on average, more than 10 and 15 points higher, respectively, when compared to the baseline model and Jais-30B. This achievement underscores the substantial value of the BiMed1.3M dataset and its unmatched effectiveness and adaptability in addressing medical queries within a bilingual framework.

TABLE 2

Performance of BiMediX on the Bilingual benchmark.

| | MMLU | | | | | | | | | |
|---|---|---|---|---|---|---|---|---|---|---|
| Model | Cli-KG | C-Bio | C-Med | Med-Gen | Pro-Med | Ana | MedMCQA | MedQA | PubmedQA | AVG |
| Jais-30B | 57.4 | 55.2 | 46.2 | 55.0 | 46.0 | 48.9 | 40.2 | 31.0 | 75.5 | 50.6 |
| Mixtral-8x7B | 59.1 | 57.6 | 52.6 | 59.5 | 53.3 | 54.4 | 43.2 | 40.6 | 74.7 | 53.0 |
| BMediX (Bilingual) | 70.6 | 72.2 | 59.3 | 74.0 | 64.2 | 59.6 | 55.8 | 54.0 | 78.6 | 65.4 |

See Sengupta et al., 2023 and Jiang et al., 2024.

Arabic Benchmark: BiMediX was evaluated using the Arabic benchmark, comparing its performance with that of Jais-30B. In Table 3, the findings for Jais and BiMediX are shown in two configurations: one pre-trained exclusively on Arabic content (Arabic) and the other with bilingual data (Bilingual). The disclosed bilingual model outperforms in all categories within the Arabic context, underscoring that the integration of both types of training data significantly enhances the understanding and processing of medical information in an Arabic setting.

TABLE 3

Performance of BiMediX on the Arabic benchmark.

| | MMLU | | | | | | | | | |
|---|---|---|---|---|---|---|---|---|---|---|
| Model | Cli-KG | C-Bio | C-Med | Med-Gen | Pro-Med | Ana | MedMCQA | MedQA | PubmedQA | AVG |
| Jais-30B | 52.1 | 50.7 | 40.5 | 49.0 | 39.3 | 43.0 | 37.0 | 28.8 | 74.6 | 46.1 |
| Ours (Arabic) | 60.0 | 54.9 | 55.5 | 58.0 | 58.1 | 49.6 | 46.0 | 40.2 | 76.6 | 55.4 |
| BiMediX (Bilingual) | 63.8 | 57.6 | 52.6 | 64.0 | 52.9 | 50.4 | 49.1 | 47.3 | 78.4 | 56.5 |

See Sengupta et al., 2023.

English Benchmark: In this section, the quantitative performance of the English model is evaluated against conventional state-of-the-art English medical models. As illustrated in Table 4, BiMediX exhibits outstanding performance across all subsets, securing the highest average scores among all models assessed. When compared to Clinical Camel-70B model, BiMediX exhibits around 10% average performance gain. Furthermore, it also outperforms Meditron-70B in almost every subset except for MedMCQA. Notably, the model's success comes without the need for separate fine-tuning on the training set for each evaluation benchmark, in contrast to Meditron, which employs individual fine-tuning for each evaluation benchmark to achieve favorable outcomes. This demonstrates the disclosed model's versatility in handling various medical interactions simultaneously. Moreover, the disclosed method outperforms Med42 by an average gain of 2.5%

TABLE 4

Performance of BiMediX on the English benchmark.

| Model | MMLU | | | | | | MedMCOA | MedQA | PubmedQA | AVG |
|---|---|---|---|---|---|---|---|---|---|---|
| | Cli-KG | C-Bio | C-Med | Med-Gen | Pro-Med | Ana | | | | |
| PMC-LLaMA-13B | 63.0 | 59.7 | 52.6 | 70.0 | 64.3 | 61.5 | 50.5 | 47.2 | 75.6 | 60.5 |
| Med42-70B | 75.9 | 84.0 | 69.9 | 83.0 | 78.7 | 64.4 | 61.9 | 61.3 | 77.2 | 72.9 |
| Clinical Camel-70B | 69.8 | 79.2 | 67.0 | 69.0 | 71.3 | 62.2 | 47.0 | 53.4 | 74.3 | 65.9 |
| Meditron-70B | 72.3 | 82.5 | 62.8 | 77.8 | 77.9 | 62.7 | 65.1 | 60.7 | 80.0 | 71.3 |
| BiMediX | 78.9 | 86.1 | 68.2 | 85.0 | 80.5 | 74.1 | 62.7 | 62.8 | 80.2 | 75.4 |

See Wu et al., 2023; Christophe et al., 2023; Toma et al., 2023; and Chen et al. 2023.

Furthermore, the disclosed model is more efficient in terms of prediction speed (latency and tokens per second) than all other models considered, as detailed in Table 5.

TABLE 5

Model statistics comparing memory size and inference speed, computed with (LLm-analysis, 2023) on GPU A100-80 GB.

| Model | Active Param | Latency | Tokens/sec |
|---|---|---|---|
| PMC-LLaMA-13B | 13B | 4.1 s | 124.1 |
| Med42-70B | 70B | 24.5 s | 20.9 |
| Meditron-70B | 70B | 24.5 s | 20.9 |
| Jais-30B | 30B | 14.0 s | 36.5 |
| Ours-BiMediX | 13B | 2.8 s | 180.6 |

See Wu et al., 2023; Christophe et al., 2023; Chen et al., 2023, and Sengupta et al. 2023.

English Dataset Composition

TABLE 6

Statistics of English datasets across QA, MCQA, and Chat (with more than one turn of exchanges) for training and testing, totaling 288.42M tokens.

| Data | Samples | Avg. Turns | #Tokens |
|---|---|---|---|
| QA | 268.2K | 1.00 | 51.5M |
| MCQA | 413.6K | 1.00 | 163.0M |
| Chat | 184.8K | 4.71 | 73.6M |
| Total | 867.8K | 1.79 | 288.4M |

TABLE 7

Statistics of the BiMed1.3M across QA, MCQA, and Chat (with more than one turn of exchanges) totaling 623M tokens and 1.3M samples. This bilingual dataset, derived from translating approximately 50% of the English dataset into Arabic, is 1.5 times larger due to its 2:1 English-to-Arabic content ratio.

| Data | Samples | Ave. Turns | #Tokens |
|---|---|---|---|
| QA | 423.8K | 1.00 | 131.8K |
| MCQA | 638.1K | 1.00 | 342.5M |
| Chat | 249.7K | 4.72 | 158.0M |
| Total | 1311.6K | 1.71 | 632.3M |

Comparison to Previous Work

Similar to ClinicalCamel, the disclosed models are fine-tuned on conversational data, with more than one turn of interactions, to significantly improve understanding and response capabilities in medical contexts. Notably, the disclosed models are the first to integrate all conceivable interaction types, including Q&A, MCQA, and Chat, into a large-scale instruction tuning dataset. Unlike models that undergo continual pretraining on the base model weights, such as PMC-LLaMA and Meditron, the disclosed methodology steers clear of this approach due to the considerable demands for additional data collection, extended training periods, and potential to impair the base model's capabilities. Furthermore, the disclosed models adopt Parameter-Efficient Fine-Tuning (PEFT) techniques to boost model performance efficiently, circumventing the need for substantial resources. A summary of conventional works is provided in Table 8.

ADDITIONAL EXAMPLES

TABLE 8

Comprehensive comparison with current open-source medical models, highlighting language, training strategy, and data statistics. PEFT indicates whether models have been adapted for specific tasks with minimal parameter updates. Chat means multi-round QA.

| Model | Language | Continual Pretraining | Instruction Tuning PEFT | Data Type | Data Size |
|---|---|---|---|---|---|
| ChatDoctor | EN | X | X | QA | 100K |
| MedAlpaca | EN | X | ✓ | QA | 160K |
| PMC-LLaMA | EN | ✓ | X | QA + MCQA | 514K |
| Clinical Camel | EN | X | ✓ | MCQA + Chat | 174K |
| Med42 | EN | — | — | — | — |
| Meditron | EN | ✓ | X | MCQA | 370K |
| Ours-BiMediX | AR & EN | X | ✓ | QA + MCQA + Chat | 1312K |

See Yunxiang et al., 2023; Han et al., 2023; Wu et al., 2023; Toma et al., 2023; Christophe et al., 2023; and Chen et al., 2023.

TABLE 9

Summary of sources.

| Dataset | Count | Description |
|---|---|---|
| Multiple-Choice Question Answering (MCQA) Datasets | | |
| PubMedQA | 210269 | Closed-answer questions from medical abstracts in PubMed research papers. |
| MedMCQA | 182822 | Multiple-choice questions from the Indian AIIMS and NEET PG medical entrance exams. |
| MedQA | 20791 | Multiple-choice questions from the USMLE for U.S. medical licensing. |
| Question Answering (QA) Datasets | | |
| HealthCareMagic | 112165 | Specialist-patient Q&As crawled from HealthCareMagic. |
| iCliniq | 7321 | Physician-patient Q&As from the iCliniq consultation site. |
| Medical Meadow | 49897 | Q&A pairs from Anki flashcards and Wikidoc's medical textbooks and Patient Information. |
| UMLS | 99057 | QAs on medical term meanings and entity relationships from knowledge graphs (Lindberg et al., 1993). |
| LiveQA | 508 | Annotated consumer health questions from the American National Library of Medicine (NLM). |
| MedicationQA | 552 | Consumer medications inquiries from MedlinePlus accompanied by manually annotated responses. |

See Jin et al., 2019; Pal et al., 2022; Jin et al., 2021; Yunxiang et al., 2023; Han et al., 2023; et al., 2023; Abacha et al., 2017; and Abacha et al., 2019.

FIGS. 10A, 10B and 10C illustrate displays for further open-ended medical-related questions and responses performed with the chat assistant in English, FIG. 11 illustrates a display for a medical-related conversation in Arabic. The example in FIG. 11 is translates as English as follows:

User: I have been diagnosed with type 2 diabetes. Can you explain how I should monitor my blood sugar levels, and what dietary changes might be necessary?

BiMediX: Monitoring blood sugar levels is crucial to controlling type 2 diabetes. It is recommended to monitor your blood sugar level at least once a day. Monitoring your blood sugar levels can help you understand how your lifestyle and diet affect your blood sugar levels. It usually requires dietary changes, such as reducing consumption of added sugar and fast-absorbing carbohydrates and increasing fiber intake, to control type 2 diabetes. It is also important to eat regular, balanced meals to help regulate blood sugar levels. I recommend discussing a blood sugar monitoring plan and diet changes with your healthcare provider.

User: I've been experiencing occasional shortness of breath and fatigue. Could these be early signs of a heart or lung condition?

BiMediX: Shortness of breath and fatigue can be early symptoms of several heart and lung conditions. This can be related to heart disease such as heart failure or coronary artery disease, or lung disease such as asthma or chronic obstructive pulmonary disease. It is important to consult with your healthcare provider to evaluate your symptoms and perform appropriate tests to determine the underlying cause. They will be able to provide an accurate diagnosis and recommend an appropriate treatment plan.

User: Is there anything I can do with my diet to help improve my situation?

BiMediX: Dietary changes can have a positive impact on heart and lung conditions. Generally, foods rich in fiber, fruits, vegetables and omega-3 fatty acids should be included in the diet. Foods to reduce your intake may include dairy products high in saturated fat, processed meats, soft drinks, and processed foods. In addition, your healthcare provider may recommend a specific diet such as a moderate-moderate diet or a low-sodium diet depending on your specific condition. It is important to consult your health care provider before making any major dietary changes to ensure your needs are met.

The types of medical interactions that BiMedX can perform, including multi-turn chats essential for follow-up inquiries with human patients, multiple-choice question answering and open-ended question answering, can be applied to telemedicine, counseling, medical diagnosis, medical research, to name a few. On the other hand, large language models are particularly vulnerable to hallucinations, toxicity, and stereotyping bias, which have been known to plague AI applications. In the general context of Large Language Models like ChatGPT, a hallucination refers to an output that is either incorrect or entirely fabricated. Toxicity refers to harmful language in digital communications, or the potential misuse of language generation that create hate speech, misinformation, or manipulation. Stereotyping bias is where an AI application reinforces harmful stereotypes. Vulnerability to hallucinations, toxicity, and stereotyping bias can have significant affect on medical tasks.

Subsequently, specialized large language models are being developed that can detect potential hallucinations, toxicity, and stereotyping bias, so that such language can be filtered out or omitted before being presented to an end user.

One of the key issues for LLMs, especially in medical contexts, is the need for high-quality, domain-specific datasets. General-purpose LLMs trained on non-specialized data often struggle with accuracy in the medical domain, as they may lack relevant knowledge or misinterpret medical information. Developing specialized medical datasets, as demonstrated by BiMediX with the creation of BiMed1.3M, an extensive bilingual dataset for Arabic and English medical interactions. This ensures that the model is fine-tuned to handle domain-specific knowledge, reducing the likelihood of misinformation or misdiagnosis.

Medical interactions occur across many languages, yet the majority of medical LLMs focus on English, limiting accessibility in regions where other languages, such as Arabic, are spoken. Multilingual capabilities in LLMs are crucial for global healthcare solutions. BiMediX has introduced a bilingual model, combining Arabic and English medical knowledge, and developed a semi-automated translation pipeline to create a robust bilingual benchmark. This can bridge language gaps and ensure wider applicability in non-English-speaking regions.

LLMs are data hungry and often use automatic data generation pipelines to be effective. However this comes with unsafe and unclean data that might influence the correctness and safety of the model predictions. BiMediX mitigates this by integrating both automated and human verification steps during dataset preparation.

LLMs can be resource-intensive, which limits their scalability in real-time diagnostic or consultation scenarios. BiMediX employs efficient fine-tuning techniques to reduce computational demands, making the model more scalable for real-world medical applications in training and prediction.

Next are details of the hardware description of the computing environment for performing the above-described medical mixture of experts machine learning and training set generation pipeline according to exemplary embodiments is described with reference to FIG. 12.

Figure 12:
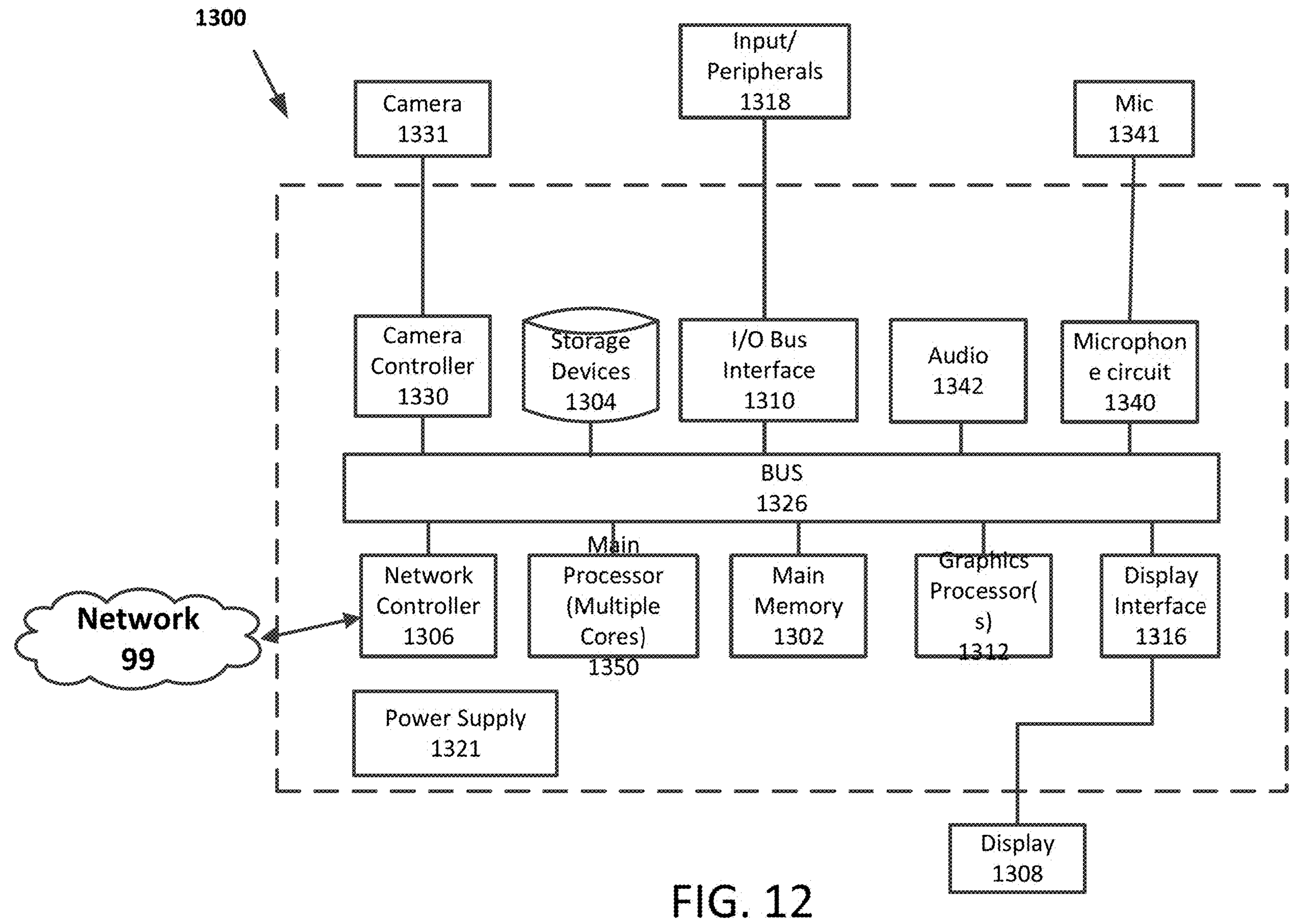
FIG. 12 is an illustration of a non-limiting example of details of computing hardware used in the computing system, in accordance with an exemplary aspect of the disclosure.

FIG. 12 is a block diagram illustrating an exemplary display system for implementing the machine learning training and inference methods according to an exemplary aspect of the disclosure. The display system may be a desktop computer, smartphone, laptop computer or smart television, as non-limiting examples. The display system includes an operating system, for example a Linux OS, Windows, a version of Unix OS, or Mac OS. The display system 1200 may include one or more central processing units (CPU) 1250 having multiple cores. The display system 1200 may include a graphics board 1212 having multiple GPUs, each GPU having GPU memory. The graphics board 1212 may perform many of the mathematical operations of the disclosed machine learning methods. The smart display system 1200 includes main memory 1202, typically random access memory RAM, which contains the software being executed by the processing cores 1250 and GPUs 1212, as well as a non-volatile storage device 1204 for storing data and the software programs. Several interfaces for interacting with the computer system 1200 may be provided, including an I/O Bus Interface 1210, Input/Peripherals 1218 such as a keyboard, touch pad, mouse, Display Adapter 1216 and one or more Displays 1208, and a Network Controller 1206 to enable wired or wireless communication through a network 99. The interfaces, memory and processors may communicate over the system bus 1226. The display system 1200 includes a power supply 1221, which may be a redundant power supply.

The display system 1200 may have extra audio-video components besides the display 1208. The extra audio-video components can include a camera 1231 for image/video capture with a camera controller circuit 1230, an audio circuit 1242 for outputting audio signals, and a microphone 1241 for inputting speech and sound signals with a microphone circuit 1240. The microphone circuit 1240 can be configured with one or more filters, such as a noise canceling filter and/or other signal processing circuitry.

In some embodiments, the display system 1200 may include a server CPU and one or more graphics cards by NVIDIA, in which the GPUs have multiple CUDA cores, and/or one or more TPUs (Tensor Processing Units). In some embodiments, the display system 1200 may incorporate a machine learning engine 1212 in a System on Chip (SoC) implementation.

The above-described hardware description is a non-limiting example of corresponding structure for performing the functionality described herein.

Numerous modifications and variations of the present disclosure are possible in light of the above teachings. It is therefore to be understood that the invention may be practiced otherwise than as specifically described herein.

The invention claimed is:

1. A computer-implemented system for medical inquiry, comprising:
- a textual input device for inputting bilingual text in both Arabic and English;
- processing circuitry configured with a mixture of experts large language model (MOE LLM) having a router network connected to a plurality of expert networks which are arranged with independent weight parameters, wherein the MOE LLM is trained with medical domain data and is configured to
- receive the input bilingual text in a format for a medical inquiry, and
- output text in a format of a response to the medical inquiry; and
- a display device for displaying the input bilingual text and the response to the medical inquiry in sequence, and
- wherein the MOE LLM of the processing circuitry is configured such that each of the expert networks are respective transformers each having a decoder and a prompt input.

2. The computer-implemented system of claim 1, wherein the textual input device is configured to input bilingual text in Unicode format.

3. The computer-implemented system of claim 1, wherein the processing circuitry is further configured to fine tune the MOE LLM using an Arabic language medical instruction set and an English language medical instruction set.

4. The computer-implemented system of claim 3, wherein the fine-tuning of the MOE LLM is configured such that the routing network routes the received bilingual text to the plurality of expert networks and determines a weighted sum of outputs of the expert networks.

5. The computer-implemented system of claim 1, wherein the transformer of each of the router network and the expert networks is configured with a trainable adapter layer attached to the decoder of the respective transformer.

6. The computer-implemented system of claim 1, further comprises:

an input for receiving English language medical instructions; and an English-to-Arabic translation pipeline in which the processing circuitry is configured with a language translation model to generate Arabic language medical instruction sets from English language medical instructions.

7. A computer-implemented system for medical inquiry, comprising:

a textual input device for inputting bilingual text in both Arabic and English;

processing circuitry configured with a mixture of experts large language model (MOE LLM) having a router network connected to a plurality of expert networks which are arranged with independent weight parameters, wherein the MOE LLM is trained with medical domain data and is configured to receive the input bilingual text in a format for a medical inquiry, and output text in a format of a response to the medical inquiry; and a display device for displaying the input bilingual text and the response to the medical inquiry in sequence;

an input for receiving English language medical instructions; and an English-to-Arabic translation pipeline in which the processing circuitry is configured with a language translation model to generate Arabic language medical instruction sets from English language medical instructions;

wherein the processing circuitry is further configured to combine the generated Arabic language medical instructions with the English language medical instructions to obtain a bilingual dataset; and fine tune the MOE LLM using the bilingual dataset.

8. The computer-implemented system of claim 6, wherein the English language medical instructions include a combination of multiple-choice question answering instructions, open-ended question answering instructions, and multi-turn question answering instructions, and wherein the processing circuitry is configured to link each multi-turn question answering dialogue to a specific multiple-choice question answering instruction.

9. The computer-implemented system of claim 6, wherein the English-to-Arabic translation pipeline of the processing circuitry is further configured to determine a translation quality value of the generated Arabic language medical instruction sets relative to the English language medical instructions, and assign scores directly proportional to the translation quality values to quantitatively assess fidelity and clarity of the generated Arabic language medical instruction sets.

10. A non-transitory computer-readable storage medium including computer executable instructions, wherein the instructions, when executed by a computer, cause the computer to perform a method of medical inquiry, the method comprising:

inputting, a textual input device, bilingual text in both Arabic and English;

training, by processing circuitry, a mixture of experts large language model (MOE LLM) having a router network connected to a plurality of expert networks which are arranged with independent weight parameters, wherein the training is with medical domain data;

receiving, by the MOE LLM, the bilingual text in a format for a medical inquiry;

outputting, by the MOE LLM, text in a format of a response to the medical inquiry; and displaying, by a display device, the received bilingual text and the response to the medical inquiry in sequence, wherein the MOE LLM of the processing circuitry is configured such that each of the expert networks are respective transformers each having a decoder and a prompt input, the method further comprising fine-tuning the MOE LLM using an Arabic language medical instruction set and an English language medical instruction set.

11. The computer-readable storage medium of claim 10, wherein the inputting, by the textual input device, bilingual text is in Unicode format.

12. The computer-readable storage medium of claim 10, further comprising routing, by the routing network, received bilingual text to the plurality of expert networks and determining a weighted sum of outputs of the expert networks.

13. The computer-readable storage medium of claim 10, wherein the fine tuning further comprises training each transformer by freezing the respective transformer encoder and decoder and training a trainable adapter layer attached to the decoder.

14. The computer-readable storage medium of claim 10, further comprises:

receiving English language medical instructions; and generating Arabic language medical instruction sets from English language medical instructions, by an English-to-Arabic translation pipeline in which the processing circuitry is configured with a language translation model.

15. The computer-readable storage medium of claim 14, further comprising:

combining, by the processing circuitry, the generated Arabic language medical instructions with the English language medical instructions to obtain a bilingual dataset; and fine tuning the MOE LLM using the bilingual dataset.

16. The computer-readable storage medium of claim 14, wherein the English language medical instructions include a combination of multiple-choice question answering instructions, open-ended question answering instructions, and multi-turn question answering instructions, the method further comprising linking, by the processing circuitry, each multi-turn question answering dialogue to a specific multiple-choice question answering instruction.

17. The computer-readable storage medium of claim 14, further comprising, in the English-to-Arabic translation pipeline of the processing circuitry:

determining a translation quality value of the generated Arabic language medical instruction sets relative to the English language medical instructions; and assigning scores directly proportional to the translation quality values to quantitatively assess fidelity and clarity of the generated Arabic language medical instruction sets.

* * * * *